US 11,645,904 B2

(12) United States Patent
Trundle et al.

(10) Patent No.: US 11,645,904 B2
(45) Date of Patent: *May 9, 2023

(54) DRONE-AUGMENTED EMERGENCY RESPONSE SERVICES

(71) Applicant: Alarm.com Incorporated, Tysons, VA (US)

(72) Inventors: Stephen Scott Trundle, Falls Church, VA (US); Alison Jane Slavin, Falls Church, VA (US)

(73) Assignee: Alarm.com Incorporated, Tysons, VA (US)

( * ) Notice: Subject to any disclaimer, the term of this patent is extended or adjusted under 35 U.S.C. 154(b) by 22 days.

This patent is subject to a terminal disclaimer.

(21) Appl. No.: 17/369,229

(22) Filed: Jul. 7, 2021

(65) Prior Publication Data

US 2021/0335123 A1 Oct. 28, 2021

Related U.S. Application Data

(63) Continuation of application No. 16/422,633, filed on May 24, 2019, now Pat. No. 11,062,589, which is a
(Continued)

(51) Int. Cl.
*G08B 25/00* (2006.01)
*H04B 7/185* (2006.01)
(Continued)

(52) U.S. Cl.
CPC .......... *G08B 25/006* (2013.01); *B60L 53/305* (2019.02); *B60L 53/36* (2019.02);
(Continued)

(58) Field of Classification Search
CPC . G08B 25/006; B60L 11/1824; B64C 39/024; B64D 47/04; B64D 47/08; G05D 1/0011; G05D 1/104
(Continued)

(56) References Cited

U.S. PATENT DOCUMENTS 6,608,559 B1 8/2003 Lemelson et al.
8,639,396 B1 * 1/2014 Hirsch ................... G05D 1/104
340/995.13
(Continued)

FOREIGN PATENT DOCUMENTS

WO WO 2015061008 4/2015
WO WO 2015108586 7/2015

OTHER PUBLICATIONS

International Search Report and Written Opinion in International Application No. PCT/US2016/055065, dated Feb. 2, 2017, 14 pages.
(Continued)

*Primary Examiner* — Muhammad Shafi
(74) *Attorney, Agent, or Firm* — Fish & Richardson P.C.

(57) ABSTRACT

Methods, systems, and apparatus, including computer programs encoded on storage devices, for drone-augmented emergency response services. In one aspect, a monitoring system, comprising: a plurality of monitoring control units, and a monitoring application server, wherein the monitoring application server includes a network interface, one or more processors, and one or more storage devices that include instructions to perform operations. The operations include receiving an emergency event notification from a first monitoring control unit of the plurality of monitoring control units, determining a type of emergency event, and a location associated with the emergency event notification, identifying one or more drones that can be deployed to the location associated with the emergency event, and transmitting an instruction to a monitoring station server associated with a drone base station to deploy the one or more identified drones to the location associated with the emergency event.

20 Claims, 12 Drawing Sheets

Related U.S. Application Data continuation of application No. 15/283,264, filed on Sep. 30, 2016, now Pat. No. 10,467,885.

(60) Provisional application No. 62/235,045, filed on Sep. 30, 2015.

(51) Int. Cl.
| | |
|---|---|
| *B60L 53/36* | (2019.01) |
| *B60L 58/12* | (2019.01) |
| *G16H 40/20* | (2018.01) |
| *B60L 53/30* | (2019.01) |
| *B64C 39/02* | (2023.01) |
| *B64D 47/04* | (2006.01) |
| *B64D 47/08* | (2006.01) |
| *G05D 1/00* | (2006.01) |
| *G05D 1/10* | (2006.01) |
| *G08B 21/04* | (2006.01) |
| *G08B 15/00* | (2006.01) |
| *G08B 13/196* | (2006.01) |
| *B64U 10/13* | (2023.01) |
| *B64U 101/30* | (2023.01) |
| *G08G 5/00* | (2006.01) |

(52) U.S. Cl.
CPC ............ *B60L 58/12* (2019.02); *B64C 39/024* (2013.01); *B64D 47/04* (2013.01); *B64D 47/08* (2013.01); *G05D 1/0011* (2013.01); *G05D 1/104* (2013.01); *G16H 40/20* (2018.01); *H04B 7/18504* (2013.01); *B60L 2200/10* (2013.01); *B60L 2200/20* (2013.01); *B60L 2240/72* (2013.01); *B64U 10/13* (2023.01); *B64U 2101/30* (2023.01); *G08B 13/1965* (2013.01); *G08B 15/00* (2013.01); *G08B 21/0423* (2013.01); *G08G 5/0069* (2013.01); *Y02T 10/70* (2013.01); *Y02T 10/7072* (2013.01); *Y02T 10/72* (2013.01); *Y02T 90/12* (2013.01); *Y02T 90/14* (2013.01); *Y02T 90/16* (2013.01); *Y02T 90/167* (2013.01); *Y04S 30/14* (2013.01)

(58) Field of Classification Search
USPC .......................................................... 701/2
See application file for complete search history.

(56) References Cited

U.S. PATENT DOCUMENTS

| | | | |
|---|---|---|---|
| 8,948,935 | B1 | 2/2015 | Peeters et al. |
| 8,983,682 | B1 * | 3/2015 | Peeters .................. G16H 40/20 701/2 |
| 9,051,043 | B1 | 6/2015 | Peeters et al. |
| 9,087,451 | B1 * | 7/2015 | Jarrell .................... G05D 1/101 |
| 9,174,733 | B1 * | 11/2015 | Burgess ................ B64C 39/024 |
| 9,373,014 | B1 * | 6/2016 | Mehranfar ......... G06K 7/10366 |
| 9,580,173 | B1 * | 2/2017 | Burgess .................... B64D 1/22 |
| 2011/0130636 | A1 | 6/2011 | Daniel et al. |
| 2014/0022051 | A1 | 1/2014 | Levien et al. |
| 2014/0254896 | A1 | 9/2014 | Zhou et al. |
| 2014/0288730 | A1 * | 9/2014 | Fucke .................... G05D 1/101 701/3 |
| 2015/0069970 | A1 * | 3/2015 | Sarkar .................... B60L 53/53 320/109 |
| 2016/0257423 | A1 * | 9/2016 | Martin .................. B64C 39/024 |
| 2016/0266577 | A1 | 9/2016 | Kerzner |

OTHER PUBLICATIONS

Di Bin et al: "Distributed Coordinated Task Allocation for Heterogeneous UAVs Based on Capacities," 2013 10th IEEE International Conference on Control and Automation (ICCA), IEEE, Jun. 12, 2013, pp. 1927-1932, XP032438877.

Extended European Search Report in European Application No. 16852804.0, dated May 15, 2019, 9 pages.

AU Examination Report in Australian Appln. No. 2021266310, dated Oct. 26, 2022, 4 pages.

* cited by examiner

900

```
┌─────────────────────────────────────────────────────────────┐
│           RECEIVE AN EMERGENCY EVENT                        │
│     NOTIFICATION ASSOCIATED WITH A PROPERTY          910    │
└─────────────────────────────────────────────────────────────┘
                              │
                              ▼
┌─────────────────────────────────────────────────────────────┐
│   DETERMINE A TYPE OF EMERGENCY AND A PROPERTY LOCATION     │
│     BASED ON THE RECEIVED EMERGENCY EVENT NOTIFICATION      │
│                                                      920    │
└─────────────────────────────────────────────────────────────┘
                              │
                              ▼
┌─────────────────────────────────────────────────────────────┐
│ IDENTIFY ONE OR MORE DRONE DEVICES THAT CAN BE DEPLOYED TO THE │
│     LOCATION ASSOCIATED WITH THE EMERGENCY EVENT            │
│                                                      930    │
└─────────────────────────────────────────────────────────────┘
                              │
                              ▼
┌─────────────────────────────────────────────────────────────┐
│      TRANSMIT A SIGNAL TO DEPLOY THE ONE OR MORE            │
│       DRONE DEVICES TO THE PROPERTY LOCATION         940    │
└─────────────────────────────────────────────────────────────┘
```

FIG. 9

DRONE-AUGMENTED EMERGENCY RESPONSE SERVICES

CROSS-REFERENCE TO RELATED APPLICATIONS

This application is a continuation of U.S. application Ser. No. 16/422,633, filed May 24, 2019, now U.S. Pat. No. 11,062,589, which is a continuation of U.S. application Ser. No. 15/283,264, filed Sep. 30, 2016, now U.S. Pat. No. 10,467,885, issued Nov. 5, 2019, which claims the benefit of U.S. Provisional Application Ser. No. 62/235,045, filed Sep. 30, 2015. All of these prior applications are incorporated by reference in their entirety.

TECHNICAL FIELD

This disclosure relates to monitoring technology using drone devices.

BACKGROUND

Security companies often provide security services to residential and commercial properties which include monitoring the properties for alarm events that may include security breaches, floods, fires, or carbon monoxide poisoning. The properties may include a security panel that communicates alarm signal information to a monitoring application server, which transmits a signal to dispatch emergency responders in response to detecting the presence of an alarm event.

SUMMARY

Techniques are described for drone-augmented emergency response services. In some implementations, a drone base station housing one or more drones may be associated with a particular neighborhood. The drone base station may deploy one or more drones to the neighborhood responsive to instructions from a monitoring application server. The application monitoring server may detect the need for drones at particular properties throughout a neighborhood based on alarm data received from one or more monitoring control units referred to as an event notification. Event notifications may include data indicative of a variety of events including security events, emergency events, or the like. The event notifications may collectively be referred to as alarm event notifications.

According to at least one aspect of the subject matter disclosed by this specification, a method, system, and apparatus, including computer programs encoded on storage devices are disclosed for implementing drone-augmented emergency response services. In some aspects, a monitoring system may include a plurality of monitoring control units, wherein each respective monitoring control unit is (i) associated with a particular property, and (ii) configured to detect an emergency event based on data received from one or more of a plurality of sensors located throughout the particular property, and a monitoring application server. The monitoring application server may include a network interface, one or more processors, and one or more storage devices that include instructions that are operable, when executed by the one or more processors, to cause the one or more processors to perform operations. In some implementations, the operations may include receiving an emergency event notification from a first monitoring control unit of the plurality of monitoring control units, determining, based on the received emergency event notification, (i) a type of emergency event, and (ii) a location associated with the emergency event notification, identifying, based on (i) the type of emergency event, and (ii) the location associated with the emergency event, one or more drones that can be deployed to the location associated with the emergency event, and transmitting an instruction to a monitoring station server associated with a drone base station housing (i) a plurality of drones that can be deployed to the location of the emergency event, and (ii) one or more charging stations for charging one or more of the drones, wherein the instruction instructs the monitoring station server to deploy the one or more identified drones to the location associated with the emergency event.

These and other versions each may optionally include one or more of the following features. For instance, the plurality of drones may include a helicopter drone, a rolling helicopter drone, or a land-based vehicle. Alternatively, or in addition, the plurality of drones may include a quad-copter drone.

In some aspects, the operations may include determining one or more drone capabilities that are related to the type of emergency event. In such instances, identifying, based on (i) the type of emergency event, and (ii) the location associated with the emergency event, one or more drones that can be deployed to the location associated with the emergency event may include identifying one or more drones that are equipped with capabilities to respond to the emergency event. In some implementations, at least one of the identified drones is a drone that is currently deployed. Alternatively, or in addition, at least one of the identified drones is a drone that is currently housed by the drone base station.

In some aspects, identifying, based on (i) the type of emergency event, and (ii) the location associated with the emergency event, one or more drones that can be deployed to the location associated with the emergency event includes identifying, based on the location associated with the emergency event, one or more drones that are within a threshold distance of the location associated with the emergency event.

In some aspects, identifying one or more drones that can be deployed based on the state of the monitoring system. The state of the monitoring system may be based on (i) the number of emergency event notifications received from the particular property and (ii) the number of emergency event notifications received from properties within a threshold distance from the particular property.

In some aspects, the emergency event notification may be based on alarm signal data from one or more sensors indicating an alarm event has been detected in a property where the first monitor control unit is located. The one or more sensors may include one or more of power sensors, smoke sensors, temperature sensors, or water sensors.

In some aspects, the operations may include receiving a request to deploy an additional drone from one or more deployed drones, and in response to receiving a request to deploy an additional drone from the one or more deployed drones, instructing the monitoring station server to deploy one or more additional drones currently based at the drone base station. Alternatively, or in addition, the operations may include in response to receiving a request to deploy an additional drone from the one or more deployed drones, instructing one or more currently deployed drones to re-deploy to the location associated with the emergency event.

In some aspects, the operations may include receiving a second emergency event notification from a second monitoring control unit of the plurality of monitoring control units, receiving a third emergency event notification from a third monitoring control unit of the plurality of monitoring control units, determining, based on the received second emergency event notification, (i) a second type of emergency event, and (ii) a location associated with the second emergency event notification, determining based on the received third emergency event notification, (i) a third type of emergency event, and (ii) a location associated with the third emergency event notification, wherein the location associated with the second emergency event is different than the location associated with the third emergency event.

In some aspects, the operations may include identifying, based on (i) the second type of emergency event, and (ii) the location associated with the second emergency event, a second set of one or more drones that can be deployed to the location associated with the second emergency event, and transmitting an instruction to the monitoring station server to deploy the second set of one or more identified drones to the location associated with the emergency event.

In some aspects, the operations may include identifying, based on (i) the third type of emergency event, and (ii) the location associated with the third emergency event, a third set of one or more drones that can be deployed to the location associated with the third emergency event, and transmitting an instruction to the monitoring station server to deploy the third set of one or more identified drones to the location associated with the emergency event.

The details of one or more implementations are set forth in the accompanying drawings and the description below. Other features will be apparent from the description and drawings.

DESCRIPTION OF DRAWINGS

FIG. 9 is a flowchart of an example of a process for deploying drones in response to a detection of a potential emergency event.

DETAILED DESCRIPTION

Techniques are described for drone assistance in emergency response services. In some implementations, drone devices operate throughout a neighborhood of multiple properties to assist in responding to emergency event notifications detected by a monitoring application server. In response to an emergency event notification, the drone devices may identify users of the property and provide assistance. In some instances, the drone devices may additionally perform routine surveillance operations and exchange data with security providers preemptively to reduce the occurrence of subsequent emergency events.

In some implementations, drone devices may be used to augment emergency response services in response to detecting an emergency event within a property. For example, a monitoring application server may receive emergency event notifications based on alarm signal data associated with a property, determine a type of emergency and a property location based on the received emergency event notification, determine that one or more drone devices are within a threshold distance from the location, and transmit a signal to a monitoring application server to deploy the one or more drone devices to the property location.

Figure 1:
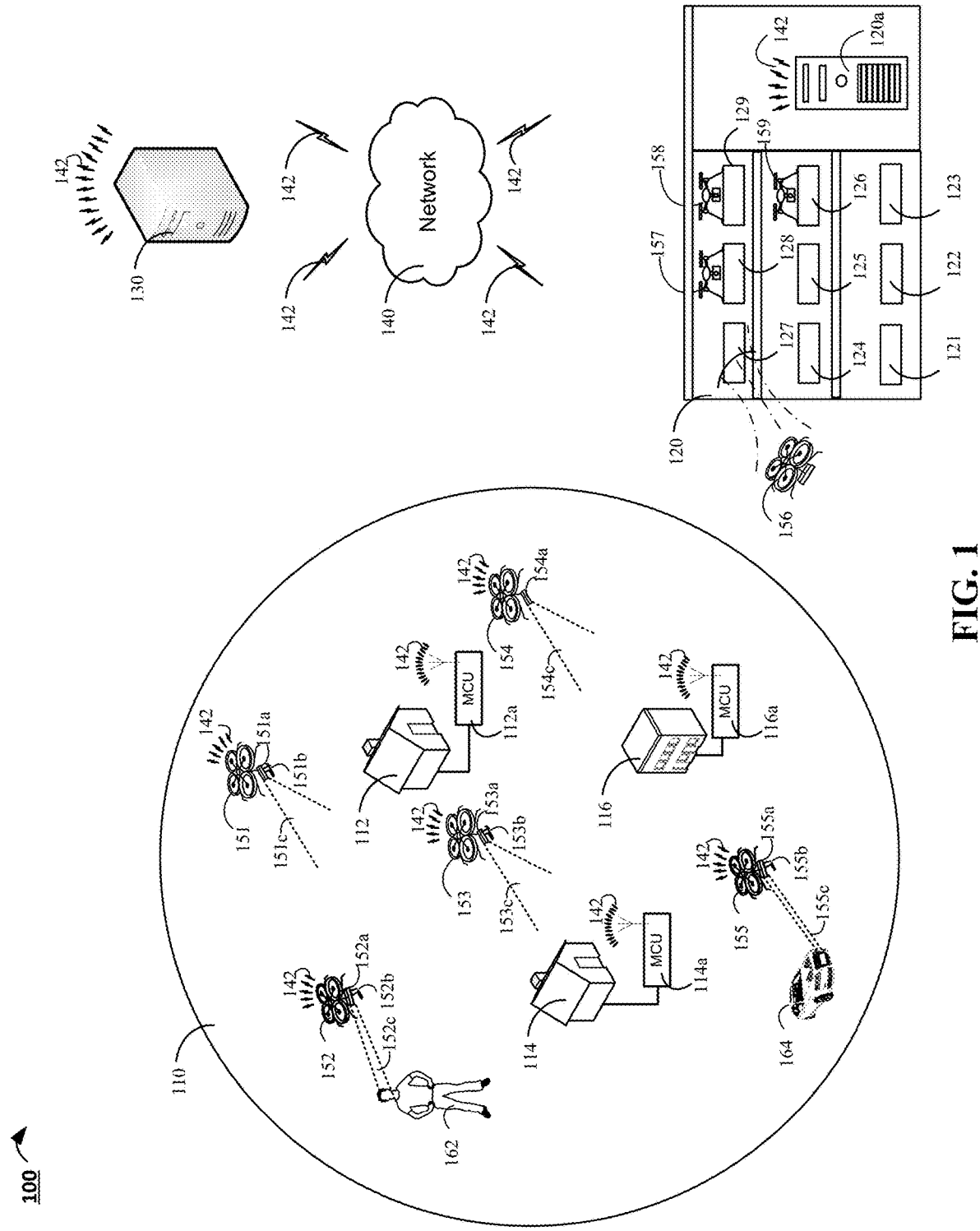
FIG. 1 is a contextual diagram of an example of a community-based drone augmented surveillance system that performs surveillance of a neighborhood.

FIG. 1 is a contextual diagram of an example of a community-based drone augmented surveillance system 100 that performs surveillance of a neighborhood 110. The drone augmented surveillance system 100 includes multiple monitor control units 112a, 114a, 116a, a drone base station 120, a monitoring application server 130, and a network 140.

The community-based drone augmented surveillance system 100 may be configured to perform surveillance operations of a neighborhood 110. The neighborhood 110 may a particular geographic region that includes multiple types of properties including residential properties 112, 114, commercial office buildings 116, or the like. In some instances, a neighborhood 110 may also include one or more public properties such as a park, a school, a university, government buildings, or the like. One or more properties in the neighborhood 110 may include a monitor control unit such as, for example, a monitor control unit 112a and one or more sensors.

A monitor control unit for a particular property such as 112a may be configured to receive event notifications from one or more of the sensors associated with the particular property. In some instances, the monitor control unit may evaluate the received event notification to determine whether the event notification is likely indicative of a potential security event, emergency event, or other type of alarm event. Alternatively, or in addition, the monitor control unit may relay received event notifications to a monitoring application server 130 via the network 140. The monitor control unit may connect to the network 140 using one or more wired, or wireless, communication links 142. Once received, the monitoring application server 130 may analyze the received event notifications to determine whether the event notification is likely indicative of a potential security event, emergency event, or other type of alarm event. Event notifications may include, for example, alarm signal data that is transmitted between any two components of an alarm monitoring system. The components of an alarm monitoring system may include sensors, monitor control units, monitoring application servers, monitoring station servers, or the like.

The monitor control unit 112a, 114a, 116a or the monitoring application server 130 may transmit instructions to a monitoring station server 120a to deploy one or more drones 151, 152, 153, 154, 155, 156, 157, 158, 159 associated with a particular drone base station 120. Instructions transmitted to the monitoring station server 120a may include, for example, information identifying the type of potential event detected by the monitoring control unit 112a, 114a, 116a or the monitoring application server 130 and a location of the detected potential event. In response to receiving the deployment instructions, the monitoring station server 120a may instruct one or more drones 151, 152, 153, 154, 155, 156, 157, 158, 159 to travel to the location of the detected potential event. The drones 151, 152, 153, 154, 155, 156, 157, 158, 159 may travel to the location of the detected potential event, and investigate the detected potential event.

The drones 151, 152, 153, 154, 155, 156, 157, 158, 159 may be based at a drone base station 120. The drone base station 120 may include one or more drones such as drones 157, 158, 159, one or more charging stations such as charging stations 121, 122, 123, 124, 125, 126, 127, 128, 129, and a monitoring station server 120a. The monitoring station server 120a may be configured to deploy, track, and service drones based in the drone base station 120 associated with the monitoring station server 120a. Servicing a drone may include, for example, ensuring that a drone's battery is sufficiently charged to perform any necessary actions required of the drone while deployed.

In some implementations, such as the implementation of FIG. 1, the monitoring station server 120a may instruct one or more drones 151, 152, 153, 154, 155, 156, 157, 158, 159 to deploy to neighborhood 110 from the drone base station 120 without an instruction from a monitoring control unit 112a, 114a, 116a or the monitoring application server 130. For instance, the monitoring station server 120a may deploy one or more drones 151, 152, 153, 154, 155, 156, 157, 158, 159, and instruct the deployed drones to perform surveillance of the neighborhood 110. For example, drones 151, 152, 153, 154, 155, 156 may be deployed to monitor the neighborhood 110. Monitoring, or surveilling, the neighborhood 110 may include the drone using one or more sensors to capture information that may be related to one or more potential security events, emergency events, or other alarm events.

In some implementations, each of the deployed drones 151, 152, 153, 154, 155, 156 may be equipped with tools 151a, 151b, 152a, 152b, 153a, 153b, 154a, 155a, 155b that can be used to perform surveillance of the neighborhood 110, engage one or more individuals who may pose a threat, or both. For instance, a drone 151 may be equipped with one or more video cameras 151a and a flashlight 151b. The video camera may capture 151c live video feeds that can be transmitted back to the application monitoring server 130 via a network 140 using one or more communications links 142. Alternatively, or in addition, the drone may use the flashlight 151b to illuminate an area, when appropriate (e.g., at night), of the neighborhood 110 so that the area of the neighborhood can be clearly viewed on the camera feed. While deployed to perform surveillance, the deployed drones 151, 152, 153, 154, 155, 156 may travel in random flight paths that systematically sweep some, or all, of the neighborhood 110. Alternatively, the deployed drones 151, 152, 153, 154, 155, 156 may be configured to travel in predetermined flight paths that cover some, or all, of the neighborhood 110.

Alternatively, or in addition, each deployed drone 151, 152, 153, 154, 155, 156 may seek out persons who are outside one or more properties within the neighborhood 110 such as person 162. Once a deployed drone such as drone 152 encounters a person such as person 162, the deployed drone may take action to determine whether the person 162 is a potential security threat. For instance, the deployed drone may use a high resolution camera 152a to perform facial recognition analysis 152c of the person 162. Alternatively, or in addition, the deployed drone 152 may perform other types of biometric analysis of the person 162 such as, for example, a retina scan, voice print, DNA test, or the like.

The deployed drone 152 may determine whether the person 162 is a potential security threat in a number of different ways. For instance, in one implementation, the deployed drone may search one or more local law enforcement databases, federal law enforcement databases, public records database, or the like, based on the obtained biometric data (e.g., facial recognition scan, retina scan, voice print, DNA test, or the like) to determine if a record corresponding to the person 162 can be found. Alternatively, or in addition, the deployed drone may search a database of authorized residents, or visitors, of neighborhood 110 to determine, based on the obtained biometric data (e.g., facial recognition scan, retina scan, voice print, DNA test, or the like), whether a record corresponding to the person 162 can be found. In some implementations, the database of known residents may include residents of the neighborhood 110 and authorized visitors to neighborhood 110. For instance, in some implementations, visitors to neighborhood 110 may be required to register with a neighborhood database when coming to visit a known resident of neighborhood 110. In such implementations, if the visitor is not registered with the neighborhood database, the visitor may be considered an unauthorized visitor to the neighborhood. Alternatively, or in addition, and unauthorized visitor to a neighborhood may include a person whose name was added to a blacklist in a neighborhood database. A person whose name is on the blacklist may also be considered an authorized visitor to the neighborhood.

If, for example, the deployed drone 152 determines in a first scenario that a record corresponding to the person 162 (i) is not found in one or more local law enforcement databases, one or more federal law enforcement databases, one or more public records database, or the like, (ii) is found in the neighborhood residents database, or (iii) both, the deployed drone 152 may determine that the person is not a potential security threat, and take no further action.

On the other hand, if the deployed drone 152 determines in a second scenario that a record corresponding to the person 152 is (i) found in one or more local law enforcement databases, federal law enforcement databases, public records database, or the like, (ii) not found in the neighborhood residents database, or (iii) both, then the deployed drone 152 may determine that the person is a potential security threat. In such instances, the deployed drone 152 may take necessary steps to mitigate the detected threat. For instance, the drone 152 may report its search result findings to the monitoring application server 130, monitoring station server 120a, or the like using the network 140 and wait for instructions regarding the type of engagement policy that the drone 152 should use to engage the person 162. In some instances, the monitoring application server 130 or monitoring station server 120a may instruct the deployed drone 152 to engage the person 162 using a particular engagement policy (e.g., a low-level engagement policy, a moderate-level engagement policy, a high-level engagement policy, or the like) based on the respective server's analysis of the drone's search result findings. For example, the monitoring application server 130 may analyze the second scenario search results indicating the person 162 has a record is found in a law enforcement database. In that second scenario, the server may determine that the record indicates that there is a warrant out for person's 162 arrest. Based on the analysis, the monitoring application server 130 may instruct the deployed drone 152 to employ a moderate-level engagement policy. Described in more detail below, a moderate-level engagement policy may include contacting law enforcement, and then trying to temporarily disable, or otherwise contain, the person 162 by playing extremely loud music, displaying extremely bright lights, or the like until law enforcement officials arrive.

In some instances, additional processing may be performed by the drone 152 or the monitoring application server 130 in order determine whether the person 162 is a threat. For example, if the deployed drone's search of a criminal database indicates that the person 162 is an ex-convict who is on parole, the deployed drone 152 may determine whether the person 162 is in violation of the person's 162 parole. Alternatively, the deployed drone 152 may merely determine that the person is an ex-convict who is on parole via the database(s) search, and request further instruction from the monitoring application server 130. In response, the monitoring application server 130 may perform additional processing to determine whether the ex-con is in violation of his/her parole, and provide instructions to the deployed drone regarding the type of engagement policy the deployed drone 152 should follow. If it is determined that the person 162 is a person in violation of his or her parole, monitoring application server 130 may instruct the deployed drone 152 to follow a moderate-level engagement policy that includes contacting local law enforcement, and taking moderate measures to disable the person 162 until law enforcement arrives, or both.

Alternatively, or in addition, in some implementations, the deployed drone 152 may request that one or more other drones assist the deployed drone 152. Such requests may be transmitted directly between drones using the network 140 and one or more communication links 142. Alternatively, or in addition, such requests may be transmitted to the monitoring application server 130, monitoring station server 120a, or the like which may each alone, or in combination, instruct one or more additional drones to assist the deployed drone 152 in engaging and disabling the person 162 until law enforcement officials arrive. The instruction may include (i) data identifying the potential threat (e.g., a facial image of a person 162 that is identified as an ex-con in violation of his/her parole, a facial image of a violent criminal, a voiceprint of a suspected burglar, an image of unauthorized visitor to the neighborhood 110, data indicative of the person's 162 unique gait, or the like), (ii) data identifying the location of the potential threat (e.g., GPS location, street address, or the like), (iii) data instructing one or more drones to deploy to the location, and (iv) a particular engagement policy that the one or more drones should follow once the one or more drones arrive at the location. The location of the potential threat may include, for example, a GPS location. In one implementations, one or more additional drones may be selected based on their (i) capabilities, and (2) the type of potential threat.

In some implementations, a deployed drone 155 may be equipped to scan the license plates of cars such as car 164 that are located within the neighborhood 110. For example, a deployed drone 155 may use a camera 155b to obtain an image of the license plate for each respective car residing within neighborhood 110. The deployed drone 155 may then search one or more local law enforcement database, one or more federal law enforcement databases, one or more neighborhood databases, or a combination therefore, to determine whether the car 164 belongs to a known criminal, or unauthorized visitor to neighborhood 110. If so, the deployed drone 155 may contact the monitoring application server 130, provide the records identified in the drone's 155 search result, and request instructions on how to proceed. The monitoring application server 130 may provide instructions regarding the engagement policy the drone 155 should employ. In this instance, since drone identified a record associated with the car in the one or more of the searched database, the monitoring application server 130 may instruct the drone to employ a moderate-level engagement policy that includes (i) contacting law enforcement, (ii) searching the vicinity of the car 164 in an attempt to identify the car's 164 owner, or (iii) both.

Each of the deployed drones such as deployed drones 152, 154 may continue to surveil the neighborhood 110 in order identify potential security events, potential emergency events, or other potential alarm events. Such potential events may be identified based on data detected using one or more sensors onboard the drone (e.g., cameras, microphones, or the like), receipt of an event notification from a monitoring control unit such as monitoring control units 112a, 114a, 116a, or receipt of a transmission from an application monitoring server 130, monitoring station server 120a, local law enforcement computer, or the like. Once a potential event is identified, one or more of the drones may be selected based on the type of potential event detected, the capabilities of the drone, the location of the potential event, and the drone's current location in proximity to the location of the potential event (e.g., it may be preferable to a select a drone that is closest to the location of the potential event in some instances).

In some instances, all available drones may be deployed to address a detected potential event. Alternatively, in other instances, only a subset of drones properly equipped to mitigate the threat associated with a potential event may be selected. Examples of selecting a subset of properly equipped drones are further discussed below.

The example described above with reference to system 100 of FIG. 1 generally describes a system where a monitor control unit 112a communicates event notifications to a monitoring application server 130, and the monitoring application server 130 instructions a monitoring station server 120a to deploy one or more drones. However, the present disclosure need not be so limited. For instance, in one implementation, the functionality of the monitoring application server 130 and the monitoring station server 120a may be performed by a single server. For instance, a single server such as monitoring application server 130 may receive/analyze event notifications and manage deployment of drones. In some of those implementations, the drone base station may house drones at the same location as the monitoring application server.

Figure 2:
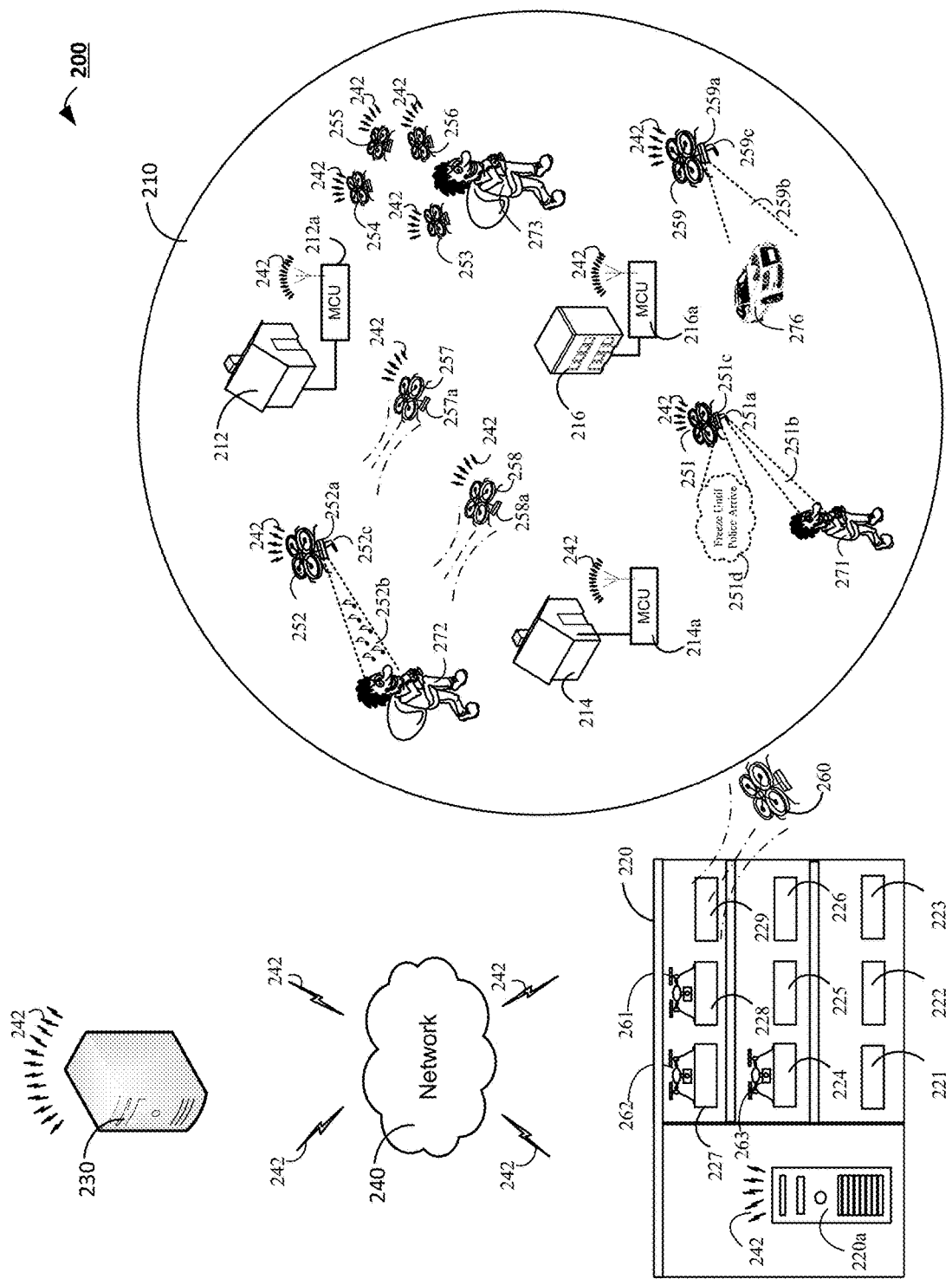
FIG. 2 is a contextual diagram of an example of a community-based drone augmented surveillance system that responds to one or more security events in a neighborhood.

FIG. 2 is a contextual diagram of an example of a community-based drone augmented surveillance system 200 that responds to one or more security events in a neighborhood 210. The drone augmented surveillance system 200 includes multiple monitor control units 212a, 214a, 216a, a drone base station 220, a monitoring application server 230, and a network 240. The system 200 is substantially similar to the system described with respect to system 100. However, the system 200 is in a state of responding to the detection of one or more security events identified by the application server 230.

During the surveillance of a neighborhood 210, a deployed drone such as deployed drone 251 may determine that a person within the neighborhood 210 is a potential threat such as a suspected criminal 272. The system 200 may determine that the suspected criminal 272 is a potential threat in any number of ways. For instance, a determination may be made by the system 200 that the suspected criminal 272 is the person who triggered the generation of a security event notification. In some implementations, one or more of the monitoring control units such as monitoring control unit 212a may relay one or more security event notifications that were generated in response to a suspected criminal's 272 incursion into the property 212.

In some instance, the security event notifications may be generated by one or more sensors associated with the property 212 in response to the suspected criminal's 272 interaction with the property 212. For instance, the suspected criminal 272 may have broken a window of a property 212, thereby triggering a glass break sensor. Alternatively, or in addition, the suspected criminal 272 may have triggered a motion sensor associated with one or more of the properties. The security event notifications may be transmitted by one or more respective sensors to a monitoring control unit such as monitoring control unit 212. Then, the monitoring control unit 212 may relay the received security event notifications to a monitoring application server 230, which analyzes the security event notifications to determine if an actual security event has occurred at the property 212. In some instances, the monitoring application server 230 may determine that an actual security event has occurred. In response, the monitoring application server 230 may instruct the monitoring station server 220a to deploy one or more drones to the property 212 to engage a person such as suspected criminal 272 who is in a predetermined vicinity of the property 212 that is generating security event notifications that have been corroborated by the monitoring application server 230.

Prior to deploying drones, the monitoring station server 220 may take steps to determine whether a potential security event exists. Determining whether a potential security event exists may include, for example, calculating a likelihood that the potential security event identified by the received security event notifications is an actual threat. If the likelihood that the potential security event is an actual security event exceeds a predetermined threshold, the monitoring station server 220a may deploy one or more drones to the neighborhood 210 to investigate the potential threat associated with the received security event notifications per the instructions received from the monitoring application server 330. Determining the likelihood that a potential security event is an actual security event may include, for example, comparing information obtained through routine surveillance of the property with current information obtained via one or more security notification events, reviewing live video feeds of the location associated with the security notification events, contacting one or more individuals present at, or near, the location associated with the security event, or the like.

Though the aforementioned example describes a system where the monitor control unit received security event notifications, and then relayed the security event notifications to the monitoring application server 230 for analysis to determine if the security event notifications are indicative of an actual security event, the present disclosure need not be so limited. For instance, in some implementations, the monitor control unit is capable of receiving, and analyzing, security event notifications in the same manner as the monitoring application server 230. In such examples, the monitoring control unit can determine whether the received security event notifications are indicative of an actual security event, and then instruct a monitoring station server 220a to deploy one or more drones to investigate the actual security event. In other implementations, the monitoring control unit may also receive security event notifications, and then relay the security event notifications to the monitoring station server 220a, which may in some implementations, perform the functionality of the monitoring application server 230 by analyzing received security event notifications to determine whether an actual security event is occurring, and then subsequently deploying one or more drones to investigate the actual security event. In some implementations, law enforcement officials may also be notified at the time of deployment of the drone.

The instruction provided to one or more drones to investigate a potential threat may also include a location the drone should travel to initially. In some instances, the location may be associated with a particular property such as, for example, property 212. This location may be determined by the monitoring application server 230 analyzing one or more security event notifications received from the monitoring control unit 212a. For instance, monitoring control unit 212a may transmit a security event notification to the monitoring application server indicating that one or more motion sensors in a property 212 have been triggered. The security event notification may include a location of the property 212 such as a GPS location, a street address, or the like. In such instances, the monitoring application server 230 transmit an instruction to the monitoring station server 220 to deploy one or more drones to travel to the property 212, and search for a suspected criminal, or other unlawful intruder, such as suspected criminal 272.

In some instances, the security event notification may not include an explicit location. In such instances, the monitoring application server 230 may determine the location of the security event based on a sensor identifier, or other data, included in the security event notification. For instance, some implementations may require that the location of each sensor be registered upon installation. Accordingly, in these implementations, the monitoring application server 230 may determine the location of a sensor by searching a database of registered sensors using the sensor identifier, or other data, that was provided in the security event notification in order to obtain the location corresponding to the received security event notification.

Alternatively, or in addition, the monitoring application server 230 may receive a series of security event notifications from multiple different sources including one or more monitoring control units, one or more video cameras strategically positioned throughout the neighborhood 210, one or more sensors (e.g., cameras, images, microphones, motion sensors, or the like) mounted to one or more drones, or the like. In some implementations, the security event notifications may include a timestamp in addition to information that can be used to identify the location of the sensor. In such instances, the monitoring application server 230 may analyze received security notification events, determine a travel path that the suspected criminal 272 is currently using to flee by analyzing each respective security event notification's location and time, and instruct one or more drones to deploy to a location that intersects the suspected criminal 272 on the suspected criminal's 272 travel path.

In some implementations, a deployed drone such as deployed drone 252 may determine that a person in the neighborhood 210 poses a potential threat independent of one or more security event notifications processed and analyzed by a monitor control unit, monitoring application server, or the like. For instance, a deployed drone 252 may perform biometric analysis of people that the deployed drone 252 encounters while performing routine surveillance of a neighborhood 210. The deployed drone 252 may perform biometric analysis by obtaining one or more biometric samples from people that the deployed drone encounters while on surveillance. For example, the drone may perform facial recognition analysis of a person such as suspected criminal 272 by capturing a high-resolution image of the person's face, and then searching one or more local law enforcement facial recognition databases, one or more federal law enforcement facial recognition databases, one or more public records facial recognition databases, one or more neighborhood facial recognition databases, or a combination thereof. Based on the results of the search, the deployed drone 252 may determine whether the person is a potential threat or not. Alternatively, the deployed drone 252 may transmit the search results to a monitoring application server 230, which can analyze the search results, and provide an instruction to the deployed drone that includes a particular engagement policy that the drone 252 should use to engage the suspected criminal 272. Though the example above discusses a deployed drone obtaining a biometric sample that includes an image of a person's face, the present disclosure need not be so limited. For instance, obtained biometric data may include any biometric data associated with a person such as an image of the person's face, a voiceprint of the person's voice, a DNA sample, or the like and search a criminal database.

A deployed drone may identify a security event, emergency event, or other alarm event in other ways. For instance, the deployed drone may capture data indicative of an emergency using one or more onboard sensors. For example, the drone may detect, using one or more microphones, that a person is screaming, yelling, or calling for help. In such instances, the deployed drone may travel to the location associated with the sound, and investigate the extent of the potential threat associated with the person who is screaming, yelling, or calling for help. Alternatively, or in addition, the drone may analyze videos, images, or the like and determining that the video, images, or the like show one or more persons fighting. In such instances, the deployed drone may travel to the location associated with the fight, and investigate the extent of the potential threat associated with the fight. Alternatively, or in addition, the deployed drone may determine that a person is walking, staggering, or crawling, in a way that doesn't match the typical pattern of the neighborhood based on an evaluation of routine neighborhood surveillance videos, images, or the like. In such instances, the deployed drone may travel to the location associated with the person is walking, staggering, or crawling in a non-routine way and investigate any associated threat.

The engagement policy that a deployed drone uses in order to engage a person may be based on the threat that the person poses. For instance, when encountering an individual in a neighborhood, a deployed drone may obtain biometric data from the individual in order to evaluate whether the person is a threat, as discussed in the example of FIG. 1. By way of example, a deployed drone may determine that the search of local law enforcement databases does not yield any hits. Alternatively, or in addition, the search of one or more federal law enforcement databases does not yield any hits. Then, a search of a neighborhood database returns search results that indicate that the individual is a resident, or authorized visitor, of a house that resides in neighborhood 210. In such instances, absent other information to the contrary, a deployed drone may determine that the individual does not pose a threat, and may continuing surveilling the neighborhood or return to a charging pad 221, 222, 223, 224, 225, 226, 227, 228, 229 in the drone base station 220. In some instances, the deployed drone may determine to employ a particular engagement policy independent of consultation with the monitoring application server 230 or central monitoring station 220. Alternatively, or in addition, the each deployed drone may be required to transmit the drones search result findings from searching one or more database to the monitoring application server 230, monitoring station server 220, or the like and await instructions as to the engagement policy that the drone should employ when the drone engages an individual who may be a potential threat.

In some instances, a deployed drone 251 may encounter a different individual in neighborhood 210 and similarly obtain 251b biometric data from the different individual 271 using a camera 251a. The result of this search may include information that indicates that there is a warrant out for the arrest of individual 271 that is associated with the obtained biometric data because of the individual's failure to pay parking tickets. Based on the information included in the search results, the deployed drone 251 may engage the individual 271 using a low-level engagement policy. A low-level engagement policy may include, for example, actions performed by a single drone that warn an individual that the individual is afoul of one or more laws, rules, or the like, notifies an enforcement agency of the violation of the law, rule, or the like, or both. Under the low-level engagement policy, for example, the drone 251 may contact law enforcement, and take one or more actions to engage the individual 271 in an effort to contain the individual until law enforcement officials arrive. Since the offense the individual 271 is suspected of is minor (e.g., failure to pay parking tickets), the deployed drone 251 may engage the individual 271 with a low level of aggressiveness. For instance, the deployed drone 251 may output an audio message 251d using an output speaker 251c that informs the individual 271 of the warrant and asks the individual 271 to stay at the individual's 271 current location until law enforcement officers arrive. In such a scenario, even if the individual 271 starts to flee, the deployed drone 251 may not pursue the individual 271 nor employ more aggressive tactics because the drone is instructed to follow a low-level engagement policy to engage individual 271 who is a low level threat.

Alternatively, another deployed drone 252 may determine that another individual is a suspected criminal 272. The deployed drone 252 may determine that the other individual is a suspected criminal 272 by obtaining the suspected criminal's 272 biometric data and searching one or more database, as described above. Alternatively, the deployed drone 252 may determine that the other individual is a suspected criminal 272 by receiving a communication from the monitoring application server 230, a monitoring station server 220a, or some other third party source such as, for example, a police department, indicating a suspected criminal 272 is residing at a particular location. For instance, a third party could transmit a notification to the drone 252 via the network 240 using one or more communication links 242 that indicates that an eyewitness spotted a suspected criminal 272 who is suspected of burglary and armed robbery on a particular street. Alternatively, or in addition, the third party may also transmit biometric data (e.g., a photograph, voice print, DNA sample, or the like) of the suspected criminal to the deployed drone 252 that the deployed drone 252 can use to biometrically identify the suspected criminal. Once the deployed drone 252 locates the suspected criminal 272 the deployed drone may confirm that the person at the particular location is the suspected criminal 272 reported by the third party using one or more of the biometric identification processes described above. For instance, the deployed drone may obtain a high-resolution image of the suspected criminal's 272 face, and compare the obtained image to the image received from the monitoring application server 230, the monitoring station server 220a, or the third party to verify the suspected criminal's 272 identity.

Based on the known facts (e.g., that the suspected criminal 272 who is suspected of committing burglary and armed robbery), the deployed drone 252 may be instructed to engage the suspected criminal 272 with a more aggressive moderate-level engagement policy. A moderate-level engagement policy may include, for example, performing one or more actions by a single drone in an attempt to temporarily contain, temporarily disable, temporarily track, or a combination thereof an individual without making physical contact. Under a moderate-level engagement policy, for example, the deployed drone 252 may use an output speaker 252a to output extremely loud audio signals 252b in an attempt to temporarily disable the suspected criminal 272 until law enforcement officers can arrive. In addition, the deployed drone 252 may use a tracking device 252c to lock onto the suspected criminal 272 and track the suspected criminal's 272 movement. Since the deployed drone 252 can track the suspected criminal's 272 movements, the deployed drone can follow the suspected criminal 272 in the event the suspected criminal start to flee. Law enforcement officials can track the deployed drone's 252 location using, for example GPS, in an effort to lead the law enforcement officers to the suspected criminal's location.

In some instances, the system 200 may use one or more of the methods described above to identify a dangerous individual such as a known terrorist 273 armed with biological weapons that poses a high-level threat to a neighborhood 210. In such instances, an instruction may be transmitted to one or more deployed drones 253, 254, 255, 256 via a network using one or more communication links 242 which instructs the one or more deployed drones 253, 254, 255, 256 to engage and contain the terrorist 273 that is located at particular location within the neighborhood 210. The instruction may be transmitted by the monitoring application server 230, a monitoring station server 220, one or more third party law enforcement servers, or the like and include the location of the terrorist, information identifying the terrorist (e.g., biometric data), or the like.

Once arriving at the terrorist's 273 location, and verifying the identity of the terrorist 273 using the methods described above, the one or more deployed drones 253, 254, 255, 256 may employ a more aggressive high-level engagement policy to engage the terrorist 273. A high-level engagement policy may include, for example, using multiple drones in an attempt to temporarily contain, temporarily disable, temporarily track, or a combination thereof an individual including the use of tactics that make physical contact with the individual. Under a high-level engagement policy, for example, the deployed drones 253, 254, 255, 256 may swarm the terrorist 273 in an effort to disorient and temporarily disable the terrorist 273. In some instances, the deployed drones 253, 254, 255, 256 may output extremely loud audio signals, extremely bright lights, or both while swarming the terrorist 273 in the effort to disorient and temporarily disable the terrorist 273. The swarm executed by deployed drones 253, 254, 255, 256 may continue until law enforcement officials arrive to apprehend the terrorist 273. One or more of the deployed drones may attempt to contain the terrorist 273 by shooting a net at the terrorist 273. If necessary, one or more of the deployed drones 253, 254, 255, 256 may crash into the terrorist 273 in an effort to knock-out the terrorist 273.

Other tactics employed by one or more of the deployed drones 253, 254, 255, 256 may include, for example, using a taser to temporarily disable the terrorist, using a paint gun to mark the terrorist (e.g., so that the terrorist can be identified later using the paint mark), using a liquid sprayer to spray foul smelling liquid on a terrorist (e.g., so that the terrorist may stink for later identification purposes), or the like.

In one or more of the aforementioned scenarios, a drone that has arrived at particular location to investigate a threat posed by an individual such as a suspected criminal, known terrorist, or the like may require additional drones to engage the potential threat. For instance, the deployed drones 253, 254, 255, 256 may transmit a request for one or more additional drones via the network 240 using a communication link 242. The request for one or more additional drones may be routed through the monitoring application server 230 or the monitoring station server 220. Alternatively, in some instances, the request for the one or more additional drones may be transmitted directly from the deployed drones 253, 254, 255, 256 to the one or more additional drones via the network 240 using one or more communications links 242. In some instances, the additional one or more drones may be drones that are already deployed such as deployed drones 257, 258 that were previously surveilling property 210. Requesting assistance from drones that are already deployed, and then re-deploying those drones, may result in faster response times than deploying a drone that is still based at the drone base station 220. Alternatively, or in addition, the additional one or more drones may be drones 261, 262, 263 that are still based at the drone base station 220.

In yet other implementations, upon receiving a request for one or more additional drones, a monitoring application server 230 or a monitoring station server 220a may select the one or more additional drones that are closest in proximity to the threat that the drone requesting help currently resides. For instance, the monitoring application server 230 or monitoring station server 220a may track the location of the drones that are currently deployed. When one of the deployed drones requests assistance from one or more additional drones, the monitoring application server 230 or monitoring station server 220a may access the location tracking information for each drone, obtain the location (e.g., GPS location) for the requesting drone, and determine the one or more drones that are closest to the requesting drone that can provide assistance. The monitoring application server 230 or monitoring station server 220a may then instruct one or more drones that are closest to the requesting drone to travel to the requesting drone's location, and provide assistance. In a similar manner, the monitoring application server 230 may instead instruct the monitoring station server 220a to re-deploy the one or more drones that are closest to the requesting drone to travel to the requesting drone's location, and provide assistance.

In some instances, an additional drone may be selected based on the additional drone's proximity to the requesting drone's location, the additional drone's capabilities, or both. For instance, the set of deployed drones 253, 254, 255, 256 swarming the terrorist 273 may determine that the swarm technique is not effective because the terrorist 273 is still active and oriented after the deployed drones 253, 254, 255, 256 have swarmed the terrorist 273 for more than a predetermined period of time. In such instances, the deployed drones 253, 254, 255, 256, may request one or more drones that can employ a more aggressive tactic to temporarily contain, temporarily disable, or both, the terrorist 273 until law enforcement arrives. For instance, the deployed drones 253, 254, 255, 256 may request one or more additional drones 257, 258 that are equipped with respective tasers 257a, 258a that can be used to taser the terrorist 273 who has been unable to be temporarily contained, temporarily disabled using other means.

One or more deployed drones such as drone 259 may surveil, investigate, and engage vehicles such as vehicle 276 in a substantially similar manner as the way that the drones surveil, investigate, and engage individuals. For instance, a deployed drone 259 may obtain identifying information for a vehicle 276 such as a license plate using a camera 259a. Then, the deployed drone 259 may search one or more databases such as a criminal database, department of motor vehicle database, a neighborhood database, a law enforcement database, or the like to determine if the vehicle's 276 license plate is associated with an owner that is not authorized to be in the neighborhood 210, potentially a threat, or both. If it is determined that the owner (or driver) of the vehicle 276 is not authorized to be in the neighborhood 210, potentially a threat, or both, the deployed drone 259 may take necessary action based on the level of the threat posed by the owner (or driver) of the vehicle 276. For example, for lesser offenses such as a vehicle that is not authorized to be in the neighborhood, the deployed drone 259 may provide an audible warning or take picture of the vehicle's license plate that can be sent to a home owner's association that can issue a ticket to the owner (or driver). However, for more moderate offenses, the deployed drone 259 may output sounds/flashing lights to get the owner (or driver) to pull over. And, for the most severe offenses, the deployed drone request one or more additional drones that can swarm the car in an effort to force the car to pull over so that the driver can be apprehended by law enforcement. Alternatively, or in addition, the deployed drone can lock-onto the vehicle 276 and track the vehicle 276 to its destination. In such instances, law enforcement may travel to the location (e.g., GPS location) of the drone that tracked the vehicle in an effort to apprehend the owner (or driver) of the vehicle 276.

Accordingly, the system 200 can be used to dynamically deploy one or more drones from a drone base station 220 to a neighborhood 210 in order to mitigate one or more potential threats. The potential threats may be detected based on an analysis of (i) one or more security event notifications received from one or more monitor control units 212a, 214a, 216a, (ii) data obtained by one or more sensors (e.g., cameras) scattered throughout the neighborhood 210, (iii) data obtained by one or more sensors mounted to one or more deployed drones 251, 252, 253, 254, 255, 256, 257, 258, 259, (iv) data on threats provided by third parties, or (v) a combination thereof. Once detected, the monitoring application server 230 can instruct the one or more drones to investigate the detected threat. The deployed drones may then verify existence of the threat, verify the identity of the individual responsible for the threat, or both. At this point, or at the time each respective drone received initial deployment instructions, the monitoring application server 230, monitoring station server 220a, or internal software running on each respective drone, may select an engagement policy, and instruct the deployed drones to engage the individual associated with the threat using a low-level engagement policy, a moderate-level engagement policy, a high-level engagement policy, or an engagement policy that falls somewhere in between each of the aforementioned policies in terms of the aggressiveness used to engage an individual.

The aforementioned example with reference to system 200 of FIG. 2 discusses searching a variety of databases based on biometric data obtained from a person to determine whether the person is a threat. The databases include, for example, local law enforcement databases, federal law enforcement databases, public records databases, neighborhood databases, or the like. However, the present disclosure need not be so limited. For instance, other types of databases may be searched in order to determine whether a person identified by a deployed drone is a detected threat. For instance, other databases may include, for example, a database storing information regarding persons with a history of substance abuse, persons with a history of mental illness, persons registered as sex offenders, or the like. In some instances, such data may be maintained in local law enforcement databases, federal law enforcement databases, public records databases, neighborhood databases, or the like. However, in other instances, the databases may be separate databases designed to track persons with specific problems such as mental health issues, substance abuse issues, sexual predator issues, or the like. Such information may be considered by a deployed drone, monitoring application server, or both in determining a threat level associated with an individual.

In some instances, data associated with an individual in a second database may be used to support the fact that an otherwise threatening individual is not a threat. For instance, an individual may appear threatening based on a determination by a deployed drone that the individual is suspiciously staggering down the street, and a local law enforcement agency database returning data that indicates that the person is an ex-convict. However, search of a mental health database may indicate that the individual suffers from a psychological illness such as, for example, schizophrenia. In such instances, the drone may transmit a notification to law enforcement for assistance that indicates that the person is simply needs help and does not pose a threat to anyone else. Such information may allow law enforcement officials to engage the individual with an appropriate level of force.

Figure 3:
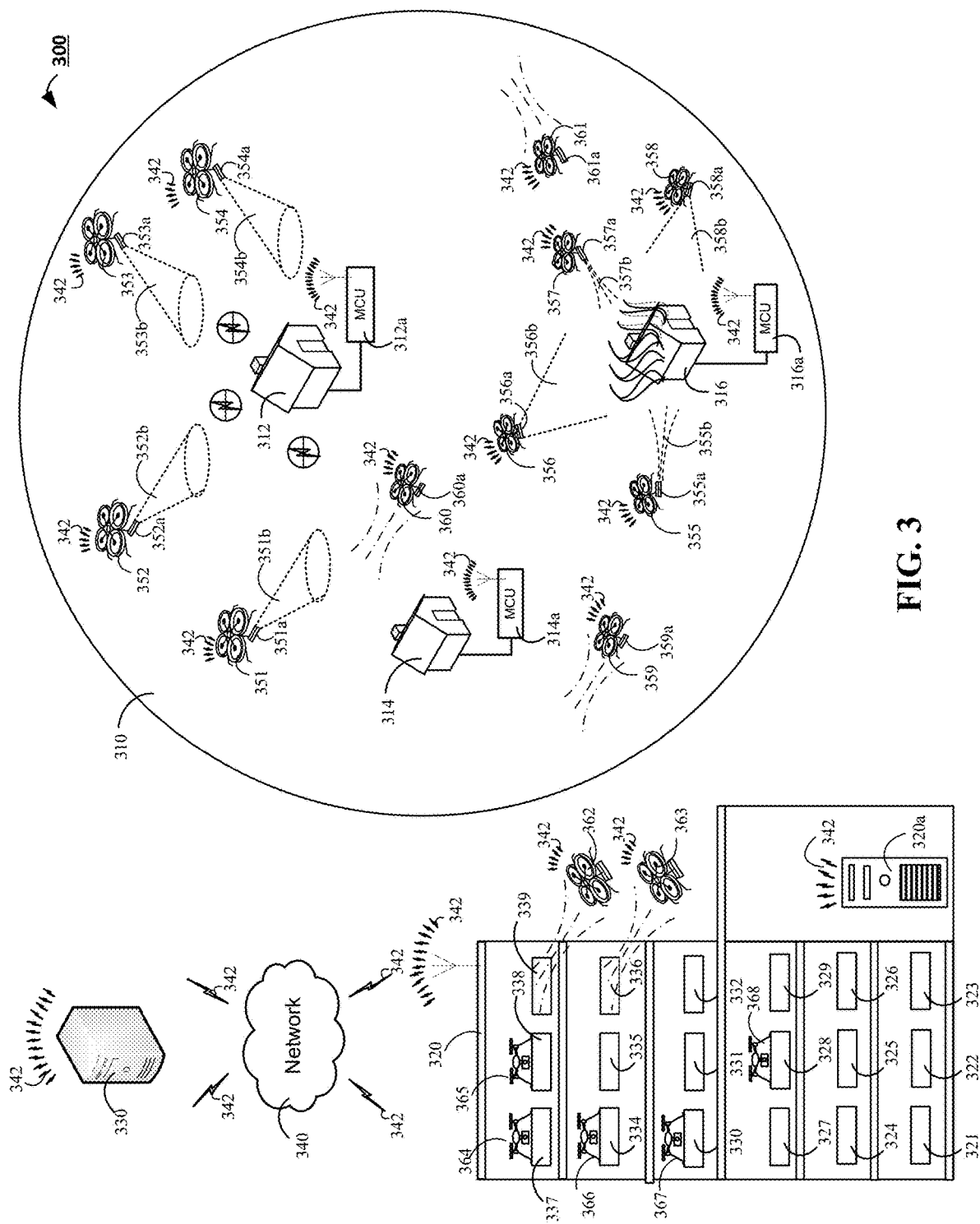
FIG. 3 is a contextual diagram of an example of community-based drone augmented surveillance system that responds to one or more emergency events in a neighborhood.

In response to the detection of a potential threat in a neighborhood 210, one or more drones may transmit instructions to one or more monitor control unit 412a, 414a, 416a. The instructions to the monitor control unit 412a, 414b, 414c may instruct the monitor control unit such as monitor control unit 412a to perform one or more actions. The actions may include, for example, lock entry doors, close/lock garage doors an electronic gates, arm security system, turn on exterior lights, initiate recording on external cameras, warn residents about a potential (or actual) threat, inform a user regarding the status of exits from the user's property, determine whether users should stay home or attempt to flee based on the type of threat, location of threat, direction threat is headed, or the like, determine if pets/kids are outside the home during a security event, notification event, and or the like FIG. 3 is a contextual diagram of an example of community-based drone augmented surveillance system 300 that responds to one or more emergency events in a neighborhood 310. The drone augmented surveillance system 300 includes multiple monitor control units 312a, 314a, 316a, a drone base station 320, a monitoring application server 330, and a network 340. The system 300 is substantially similar to the system described with respect to systems 100 and 200. However, the system 300 is in a state of responding to the detection of one or more emergency events identified by the application server 330.

Each property 312, 314, 316 may include one or more sensors that are capable of detecting events. An event may include, for example, any action that occurs in a property that triggers a sensor to transmit an event notification to a monitor control unit. In some implementations, the one or more sensors may include glass break sensors, contact sensors, motion sensors, or the like that may generally be focused on security. For instance, glass break sensors, motion sensors, or the like may be strategically placed throughout a property such as property 312, 314, 316 with the intention of detecting break-ins by one or more individuals. However, other types of sensors may be strategically placed through a property such as property 312, 314, 316 for the purpose of detecting emergency events. Such other types of emergency prevention sensors that may be strategically placed throughout a property 312, 314, 316 for the purpose of detecting emergencies may include, for example, one or more smoke detectors, one or more temperature sensors, one or more carbon monoxide detectors, gas sensors, one or more air quality sensors, one or more power detectors, or the like. In some instances, a sensor may be used for dual purposes. That is, a particular sensor of the one or more sensors may be strategically placed to detect both emergency events, security events, and potentially other types of events.

In some instances, an emergency prevention sensor may detect the existence of a potential emergency. For instance, one or more power sensors in the property 312 may determine that there is no power at property 312, one or more smoke detectors may determine that smoke is present inside the property 316, or the like. In response to detecting the existence of a potential emergency, each respective emergency prevention sensor may generate an emergency event notification, and transmit the respective emergency event notifications to a monitor control unit. For example, a power sensor at property 312 may generate an emergency event notification, and transmit the emergency event notification to the monitor control unit 312a via the network 340 using one or more communications links 342. Similarly, for example, a smoke detector in property 316 may generate an emergency event notification, and transmit an emergency notification to the monitor control unit 316a via a network 340 using one or more communications links 342.

The emergency event notifications may include information indicating the emergency type that is associated with the emergency event notification. The emergency type may include an emergency event identifier that the monitor control unit 314a, 316a, monitoring application server 330, or monitoring station server 230a can map to a particular emergency event such as, for example, smoke, fire, power outage, water leak, flooding, or the like. Alternatively, or in addition, the emergency event notification may include a sensor identifier. In such implementations, the monitoring application server 330 may include a mapping function that maps the sensor identifier to a particular type of emergency. For example, the monitoring application server 330 may determine that the emergency is fire if an emergency event notification is received that includes a sensor identifier that corresponds to a smoke detector. Each of the mapping functions described above may be implemented, for example, using one or more look-up tables.

The emergency event notifications include information indicating the location where the emergency event notification originated. For example, in one implementation, the emergency event notification may include location data such as a GPS location, a street address, or the like. Alternatively, however, the location of an emergency event may be determined without an explicit inclusion of a location in the emergency event notification. In such implementations, the location of each sensor may be registered and stored in the monitoring application server 330 at the time of installation (or at some point in time after installation). Accordingly, an emergency event notification may only include a sensor identifier, which the monitoring application server 330 can use to retrieve the location where the sensor that generated the alarm event notification is located and/or data indicative of the type of sensor.

In some implementations, the respective monitor control units 312a, 314a, 316a may relay any received emergency event notifications to the monitoring application server 330. Once received, the monitoring application server 330 may analyze the received emergency event notifications to determine the type of emergency, type(s) of drone capability needed assist in responding to the emergency, and the location of emergency.

Determining the type of emergency event may include obtaining information describing the type of emergency event from the received emergency event notifications. In one implementation, the type of emergency event information may include, for example, an emergency event identifier comprised of one or more numbers, alphabetic characters, or both that can be mapped to a particular emergency. The mapping between emergency event identifiers and emergencies may be a one-to-one mapping such that each emergency event identifier is associated with a particular type of emergency. Alternatively, or in addition, the emergency event notification may include a sensor identifier that can be used to determine the type of emergency. For example, the monitoring application server may determine that a sensor identifier corresponds to a power sensor. Accordingly, an emergency event generated by the power sensor may be determined to be a power outage. Implementations that use a sensor identifier to determine the type of emergency may not need to include an emergency event identifier whose sole purpose is to identify an emergency type, as the sensor identifier can be used for this purpose, as described above.

In a similar manner, the monitoring application server 330 can determine a set of one or more drones that have the capabilities for responding to the particular emergency associated with a property. For example, the monitoring application server 330 may include a mapping of emergencies to drone capabilities. In some implementations, this emergency to drone capabilities mapping may include a one-to-one mapping. However, in other implementations, the emergency to drone capabilities mapping may include a one-to-many mapping as there may be multiple drone capabilities that may be useful in responding to a particular emergency.

Once the monitoring application server 330 determines the emergency type, the monitoring application server 330 may instruct the monitoring station server 320a to deploy a set of one or more drones to the location associated with the emergency event that have a particular set of capabilities to the location associated with the emergency event notification. Once the deployed drones arrive at the location associated with the emergency event notification, the deployed drones may perform their respective tasks in order to assist with the response to the detected emergency.

In some implementations, the monitoring application server 330 may instruct the monitoring station server 320*a* to deploy a set of one or more drones that is selected based on the state of the surveillance system 300. A state of the surveillance monitoring system 300 may be determined based on the number of alarm event notifications from a particular property, the number of alarm event notifications received from other properties within a threshold distance from the particular property, or both. For instance, if the monitoring application server 330 has received emergency event notifications indicating that only a single sensor in a property 316 has detected smoke, the monitoring application server 330 may only instruct the monitoring station server 320*a* to deploy a single drone equipped with a camera to the property 316 to determine additional information about the emergency event notification. Alternatively, however, if the monitoring application server 330 has received multiple emergency event notifications indicating that multiple sensors in the house 316 have detected smoke and multiple sensors in the house have detected extremely high temperatures, then the monitoring application server 330 may instruct the monitoring station server 320*a* to deploy a set of multiple drones to the property 316 where the set of multiple drones is fully equipped to assist in fighting a fire. In such instances, the monitoring station server 320*a* may be instructed to deploy drones with water tanks and sprayers, tanks of sodium bicarbonate and sprayers, video cameras, and the like. In some situations, the monitoring application server 330 may determine that the state of the neighborhood monitoring system is extremely severe. For instance, a situation may arise where monitoring application server 330 receives emergency event notifications indicating smoke and high temperatures from multiple properties in the same vicinity within the neighborhood 310. In such instances, the monitoring application server 330 may instruct the monitoring station server 320*a* to deploy all drone devices capable of fighting a fire or providing assistance to other drones or law enforcement fighting a fire.

By way of example, with reference to FIG. 3, the property 312 may include one or more power sensors located throughout property 312. At least one of the power sensors may detect that power has stopped being provided to a power outlet associated with the power sensors. In response to detecting the power stoppage, the power sensors generate a respective emergency event notification that includes an emergency type identifier, a sensor identifier, or both that is transmitted to the monitor control unit 312*a*, and then relayed by the monitor control unit 312*a* to the monitoring application server 330 via the network 340 using one or more communication links 342. The monitoring application server 330 may determine using the emergency type identifier or the sensor identifier that property 312 is experiencing a power outage. The monitoring application server 330 may use the emergency type (e.g., power outage) to determine that one or more drones should be deployed to the location associated with the power sensor that is reporting a power outage. In one implementation, the monitoring application server 330 may identify a set of one or more drones that should be deployed based on the drone's capabilities for assisting with a power outage. For instance, the monitoring application server 330 may determine, based on the power outage emergency type, that a set of one or more drones should be deployed that are equipped with lights than can be used to illuminate the property 312 until power is restored. The monitoring application server 330 may use the sensor identifier to search a database of registered sensors in order to obtain the location of the power sensor that is reporting a power outage. Then, the monitoring application server 330 may transmit an instruction to the monitoring station server 320*a* via the network 340 using one or more communications links 342 that instructs the monitoring station server 320*a* to deploy one or more drones equipped with lights to illuminate the property 312.

The deployed drones 351, 352, 353, 354 may each use a respective light 351*a*, 352*a*, 353*a*, 354*a* to illuminate 351*b*, 352*b*, 353*b*, 354*b* the property 312, for example, during periods of the day without natural sunlight until power can be restored. In some instances, as necessary, the deployed drones 351, 352, 353, 354 may provide assistance to power station workers who need to travel to property 312, or its vicinity, in order to fix power lines, transformers, or the like to resolve the power outage. For instance, the deployed drones may illuminate the areas where the power station workers are working, transport in portable generators, provide live video feeds to the power station workers at remote locations, provide live video feeds to government officials highlighting the power outage recovery efforts, or the like. In some instances, one or more additional drones 362, 363 may be requested to assist in the power outage recovery efforts as needed.

By way of another example, with reference to FIG. 3, the property 316 may include one or more smoke sensors located throughout property 316. At least one of the smoke sensors may detect the presence of smoke with the property 316. In response to the detection of smoke, the smoke sensors may generate a respective emergency event notification that includes an emergency type identifier, a sensor identifier, or both that is transmitted to the monitor control unit 316*a*, and then relayed by the monitor control unit 316*a* to the monitoring application server 330 via the network 340 using one or more communication links 342. The monitoring application server 330 may determine using the emergency type identifier or the sensor identifier that property 316 is experiencing a fire. The monitoring application server 330 may use the emergency type (e.g., fire) to determine that one or more drones should be deployed to the location associated with the smoke sensor that is reporting the presence of smoke. In one implementation, the monitoring application server 330 may identify a set of one or more drones that should be deployed based on the drone's capabilities for assisting with a fire. For instance, the monitoring application server 330 may determine, based on the fire emergency, that a set of one or more drones should be deployed that are equipped with (i) water tanks and water sprayers, (ii) fire extinguishers including $CO_2$ tanks, sodium bicarbonate tanks, or potassium bicarbonate tanks and a respective sprayer, (iii) video cameras, or a (iv) combination thereof. The monitoring application server 330 may use the sensor identifier to search a database of registered sensors in order to obtain the location of the power sensor that is reporting the presence of smoke. Then, the monitoring application server 330 may transmit an instruction to the monitoring station server 320*a* via the network 340 using one or more communications links 342 that includes the location of property 316 and instructs the monitoring station server 320*a* to deploy one or more drones equipped with (i) water tanks and water sprayers, (ii) fire extinguishers including $CO_2$ tanks, sodium bicarbonate tanks, or potassium bicarbonate tanks and a respective sprayer, (iii) video cameras, or a (iv) combination thereof to assist with putting out the fire at property 316.

The deployed drones 355, 356, 357, 358 may travel to the property 316, and assist with efforts to put out the fire at the property. For instance the deployed drone 355 may use a fire extinguisher 355a to spray sodium bicarbonate 355b on portions of the house that are burning. Alternatively, or in addition, another deployed drone 357 may use a water sprayer 357a to spray water 357b on the fire. The deployed drones 355, 357 may be able to fly into openings on the exterior of the house (e.g., broken windows, open doors, or the like) in order to search for survivors trapped inside the property 316, disperse water, sodium bicarbonate, or the like on flames burning inside the property 316. At the same time, deployed drones 356, 358 may assist with monitoring the progress being made in combating the fire by setting up a live video feed to the monitoring application server 340, the monitoring station server 320a, a fire station, a government official's office, or the like that can be viewed by human operatives. Alternatively, or in addition, the live video feed may be streamed to one or more mobile devices of a security analyst, drone base station 320 operator, a fireman, a government official, or the like.

In addition to assisting officials in monitoring the situation, one or more deployed drones may also provide assistance by delivering supplies to the scene of an emergency event. For example, one or more drones could be used to, for example, drop off gas masks, oxygen tanks, or the like to first responders. Alternatively, or in addition, one or more drones could be used to fly into a burning building and deliver gas masks, oxygen masks, or the like to victims trapped inside a burning property such as property 316. Such actions may allow the victims trapped inside the burning property to stay conscious until help arrives.

As the deployed drones 355, 356, 357, 358 begin to assist with combatting the fire at property 316, it may be determined that additional assistance is needed. As a result, one or more of the deployed drones 355, 356, 357, 358 may request the assistance of the deployed drones 359, 360, 361 in combatting the fire. For instance, over time, additional drones 359, 360, 361 that have full tanks of sodium bicarbonate 359a, 360a, water 361a, or the like may be needed to reinforce one or more drones who have already fully dispersed the contents of their respective sodium bicarbonate tanks, water tanks, or the like. The deployed drones may continue to assist in combatting the fire at property 316 until the fire is fully extinguished. The additional drones may be requested from a set of drones that are already deployed in neighborhood 310 or from a set of drones that are currently based at the drone base station on one or more charging stations 321, 322, 323, 324, 325, 326, 327, 328, 329, 330, 331, 332, 333, 334, 335, 336, 337, 338, 339. The additional drones may be requested and deployed in the same, or similar, manner as that set forth in the description of FIG. 2.

In some implementations, one or more of a deployed drone, monitoring application server, monitor control unit can communicate with members of the community where an event such as an emergency event that has occurred. In one example, one or more specific persons in the neighborhood may be identified by the drone (e.g., by searching a neighborhood database) as having a special ability such as combat training, special ops background, retired police, or the like. In such instances, a deployed drone, for example, may instruct the person identified as having a special ability to help out with an emergency event while the drone searches the neighborhood to warn other people of the emergency event who are at greater risk than the person identified as having a special ability. The users with a special ability may be directed to locations of high-risk within a property to help with protecting at-risk individual form further harm. The users with a special ability may live in a neighborhood surveilled by the drones, or just be nearby a portion of a property that is being surveilled by the drones.

Figure 4:
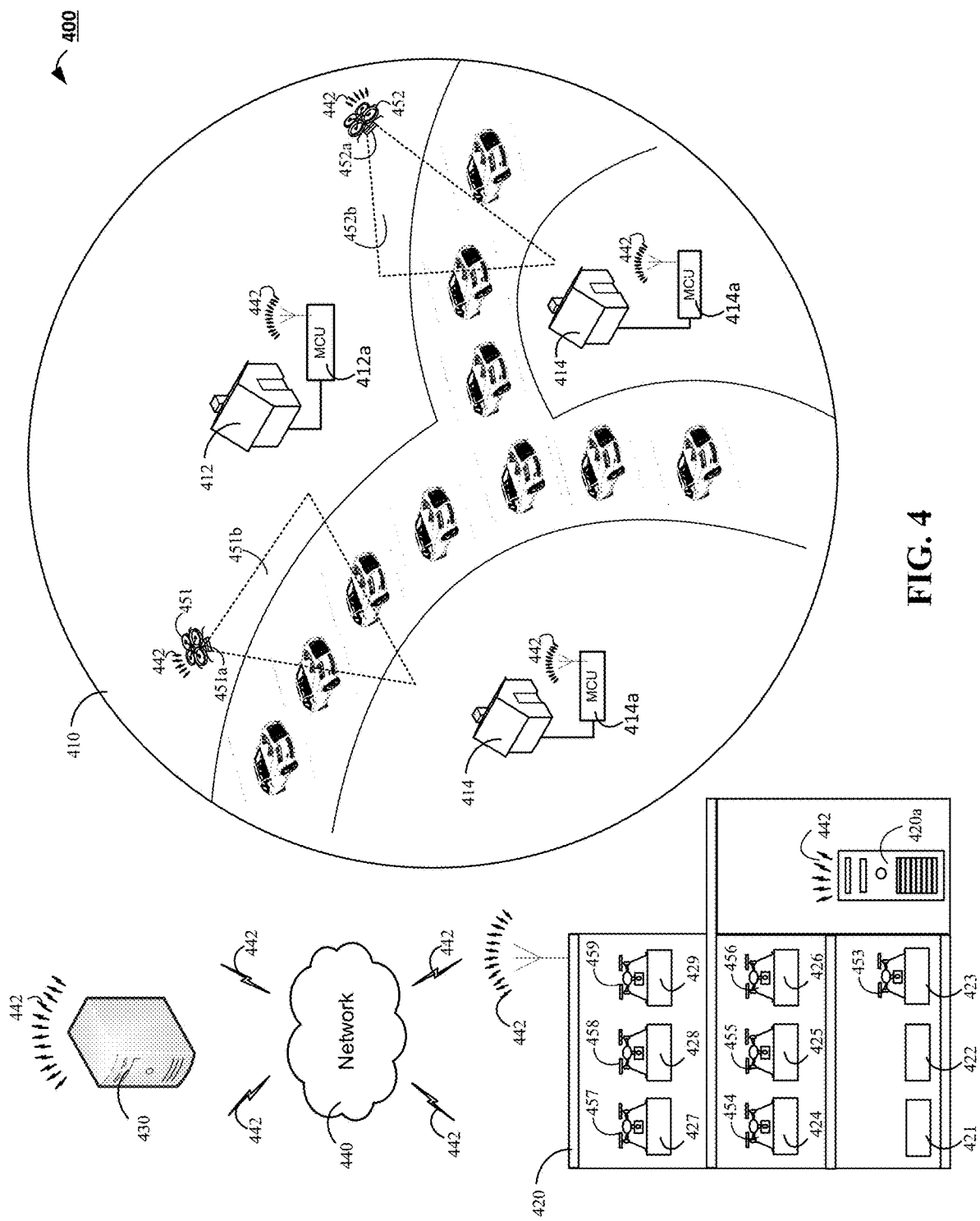
FIG. 4 is a contextual diagram of an example of a community-based drone augmented surveillance system that gathers information regarding the routines of residents in a neighborhood.

FIG. 4 is a contextual diagram of an example of a community-based drone augmented surveillance system 400 that gathers information regarding the routines of residents in a neighborhood 410. The drone augmented surveillance system 400 includes multiple monitor control units 412a, 414a, 416a, a drone base station 420, a monitoring application server 430, and a network 440. The drone base station 420 may base one or more drones 453, 454, 455, 456, 457, 458, 459 and include one or more charging stations 421, 422, 423, 424, 425, 426, 427, 428, 429. The system 400 is substantially similar to the system described with respect to systems 100, 200, and 300. However, the system 400 is employing one or more drones to gather information regarding the routines of residents in a neighborhood 410.

Periodically throughout routine days, the monitoring station server 420a may instruct one or more drones 451, 452 to deploy, and travel to the neighborhood 410. The monitoring station server 420a may instruct the deployed drones 451, 452 to gather information related to the routines of residents within the neighborhood 410. The gathered information may include, for example, video recordings of traffic patterns. For example, a drone 451 may use a camera 451a to obtain 451b video recordings of the traffic patterns that exist in neighborhood 410. The deployed drones 451, 452 may work together to aerially traverse each roadway for a particular neighborhood 410 and obtain 451b, 452b video of the traffic patterns using their respective cameras 451a, 452a. In addition to live video, the deployed drones 451, 452 may also capture still images of the traffic patterns. The capture video, images, or both may be transmitted to the monitoring station server 420a via the network 440 using one or more communications links 442. The monitoring station server 420a may later use the capture video, images, or both to verify that a potential security event or a potential emergency event is an actual security event or actual emergency event. For instance, live video feeds of a neighborhood 410a at the time of a potential security event or potential emergency event may be compared to the stored video feeds of the neighborhood during a routine day. If the result of the comparison of the video feeds indicates that the feeds are generally the same, that result may be supportive of a conclusion that the potential security event or the potential emergency event is not an actual security event or actual emergency event. On the other hand, if the result of the comparison of the video feeds indicates that the live feed video of the neighborhood 410 is different than the stored video feed for the neighborhood 410, such a result may be supportive of a conclusion that the potential security event or the potential emergency event is an actual security event or an actual emergency event.

The gathering of video (or still images) of neighborhood traffic patterns may be achieved at different times of each day of the year. The gathered video (or still images) may be stored in a database that facilitates access to the historical traffic patterns on particular days, and at particular times on each respective day. For instance, the drones may capture video of the traffic pattern every hour, of every day, and store the captured video in a database. The stored video may be tagged with a neighborhood identifier, day, street name, and timestamp indicative of the time the video was obtained by a drone, a combination thereof, or the like. Then, prior to deploying one or more drones in response to a potential security event or a potential emergency event, a monitoring station server 420a may access the database of videos, and compare the live video feed obtained as the potential security event or emergency event is going on with the stored historical video from the same general time period (e.g., within an hour, half hour, 15 minutes, or the like) on the same day for the same neighborhood in the past. Then, the result of the comparison of the live video feed to the historical video feeds can be evaluated to determine whether the results of the comparison is supportive of the existence of an actual security event or actual emergency event, or supportive of the non-existence of an actual security event or actual emergency event.

In some implementations, the system may be configured to detect, and account for, the changes in traffic patterns that occur on holidays that occur year in and year out but on different days such as memorial day, labor day, or the like. That is, the system may, for example, be able to access a calendar, and determine whether the day on which video, images, or the like is captured is a holiday. If so, it can be determined whether the traffic patterns, or other routines, identified for that particular day, are routine for a particular holiday as opposed to merely determining whether the traffic patterns identified are routine for that particular day of the week.

The examples above discuss the gathering of information regarding the routine of residents with respect to the capturing of video or images of neighborhood traffic patterns. However, the scope of the present disclosure should not be so limited. Instead, other types of information may be gathered regarding the routine of residents within a neighborhood. For example, aerial video (or images) of other portions of neighborhood may also be captured. For instance, video (or images) of sidewalk traffic, bike paths, common areas such as parks, or the like may also captured. Other types of information may also be captured that is indicative of the routines of a neighborhood on a particular routine day.

In some implementations, the gathered information regarding the routine of residents within the neighborhood may be used to detect the existence of potential problems in a neighborhood 410 by using the gathered information to detect aberrations within the neighborhood 410. For instance, the monitoring application server 430 or the monitoring station sever 430a may include an aberration engine. The aberration engine may receive as inputs gathered information regarding the historical routines of residents within the neighborhood 410 and live information that is being collected regarding the current behavior of residents within the neighborhood 410. The aberration engine may identify one or more aberrations that exist between the historical information and the current information. In response to a detected aberration, one or more drones may be deployed in order to investigate the location of the neighborhood 410 that is associated with the aberration.

In some implementations, there may be times when monitoring application server of system 400 isn't sure whether something represents an aberration even after comparing current sensory/video data to historical data. In such instances, the system may continue to gather more data over time so they can make a better determination. For example, a drone may capture video or images that can be streamed to the monitoring application server that shows a person up a tree near a house, and isn't sure if that is normal or not. In such instances, the monitoring application server 430 may instruct one or more drones in the system to come back periodically to collect more sensor data and footage with the goal of making a determination about what is happening and whether to alert users and/or responders. Over time, as more video and images of the location is determined, it can be determine if the person in the tree is a resident of the property the tree is near, the approximate age of the person, the gender of the person, the identity of the person (using databases identified above), and thereby make a determination as to whether there is a threat, there is not threat, or the like. Alternatively, if after a predetermined period of time has passed and more data has been collected, the apparent aberration has not be correctly interpreted, the monitoring application server 430 may escalate the issue to humans at drone base station for further consideration.

Figure 5:
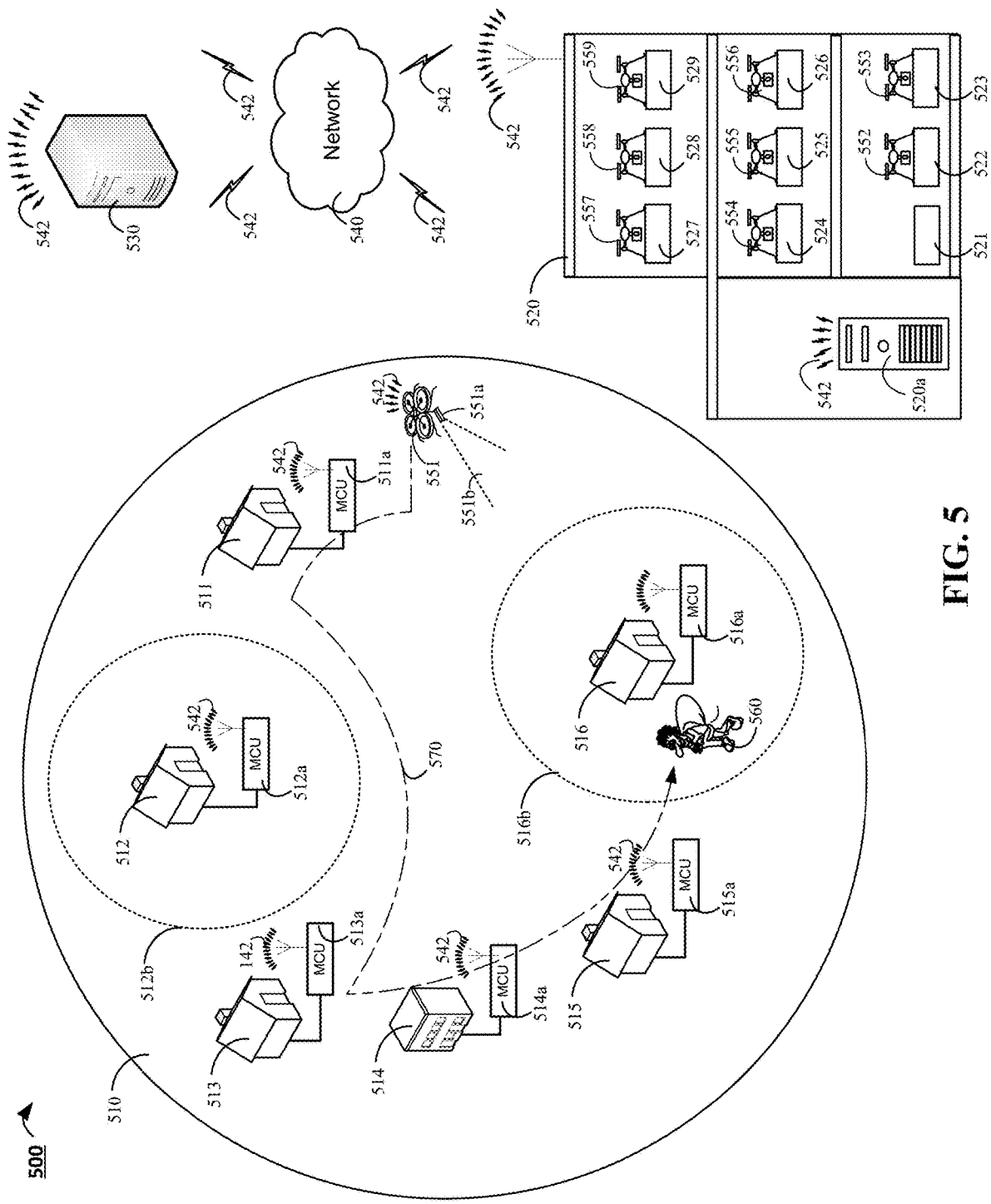
FIG. 5 is a contextual diagram of an example of community-based drone augmented surveillance system that selectively monitors properties in a neighborhood based on user account settings.

FIG. 5 is a contextual diagram of an example of community-based drone augmented surveillance system 500 that selectively monitors properties in a neighborhood 510 based on user account settings. The drone augmented surveillance system 500 includes multiple monitor control units 511a, 512a, 513a, 514a, 515a, 516a, a drone base station 520, a monitoring application server 530, and a network 540. The drone base station 520 may base one or more drones 552, 553, 554, 555, 556, 557, 558, 559 and include one or more charging stations 521, 522, 523, 524, 525, 526, 527, 528, 529. The system 500 is substantially similar to the system described with respect to systems 100, 200, 300, and 400. However, the system 500 is employing one or more drones to perform surveillance of neighborhood 510 based on user account settings.

In some implementations, a resident of neighborhood 510, lawful property owner of a property that resides within neighborhood 510, or a lawful occupant of a property residing within the neighborhood 510 (collectively referred to as "resident") may customize drone surveillance of resident's property. For instance, the monitoring application server 530, or some other third party server, may host a portal that is accessible via the network 540 that provides the resident with access to the resident's user account. The resident's user account may include a profile of one or more customizable drone surveillance settings. Customizable drone surveillance settings may include one or more attributes that the resident can assign a value to in an effort to control the level of drone surveillance that is performed with respect to the resident's property. For example, a user may access the customizable drone surveillance settings in order to toggle one or more specific customizable drone surveillance settings such as (i) whether a drone can (or cannot) record video of the resident's property, (ii) whether a drone can (or cannot) capture still images of the property, (iii) whether a drone can (or cannot) perform thermal imaging of the property, (iv) whether a drone can (or cannot) enter the within a predetermined distance of the resident's housing structure, (v) whether a drone can (or cannot) cross the resident's property line, (vi) whether a drone can (or cannot) enter the airspace above the resident's property, or the like.

In some implementations, the customizable drone surveillance settings may be conditional. For instance, a resident may set one or more customizable drone surveillance settings which can be overridden in the event a predetermined condition is detected. For example, a resident may configure the resident's user account such that a drone cannot enter the airspace of the resident's property unless one or more security event notifications, emergency event notifications, or one or more other alarm event notifications have been generated by a sensor associated with the resident's property. Such conditions may be set in place by a resident of the property in order to prohibit a drone from regularly surveilling the resident's property while the resident still receives the benefits of the community drone surveillance system when the resident's property is undergoing a security event or an emergency event.

It is contemplated that any number of customizable drone surveillance settings, corresponding conditions on the customizable drone surveillance settings, or combinations thereof fall within the subject matter of this specification. Other examples of conditional drone surveillance settings may include (i) permitting a drone to capture video or image surveillance of a particular portion of the resident's property (e.g., permit video surveillance of back yard but not front yard), (ii) permitting a drone to capture video or image surveillance of the resident's property during particular times of the day (e.g., permit drone surveillance at night but not during the day), (iii) permitting the full scope of drone surveillance services in the event that a security event notification, emergency event notification, or any other alarm event notification is generated by any property in the same neighborhood as the resident's property, (iv) only allow surveillance of the property only if an authorized occupant of the property is not present at the property or not, (v) only allow surveillance of the property if the kids are at home and the parents are not home, or the like. In those instances where drone surveillance is contingent of the authorized occupant, parent, or the like being present at the property, the authorized occupant's, parent's, or the like location may be determined based on the location of the authorized occupant's, parent's, or the like phone, car, past geofence crossings, direct drone sighting or surveillance, or the like.

The customization of one of the one or more customizable drone surveillance settings may impact the flight path of a drone during routine drone surveillance operations or during drone response to security events or emergency events. For instance, as a drone approaches a property on the drone's flight path, the drone may access a user profile associated with the property's resident, and adjust the drones' flight path and surveillance operations based on the settings in the user profile associated with the property's resident. In one implementation, the drone may utilize a navigation map that associates resident user profile identifiers with properties on the map. The user profile identifiers may include, for example, a resident's account number. As the drone moves within a predetermined threshold distance from the property line of the resident's property, the drone may use the resident's account number to access the resident's customizable drone surveillance settings, and adjust the drone's flight path accordingly.

For example, with reference to FIG. 5, a drone 551 may be deployed by a drone base station 520 to perform surveillance of the neighborhood 510. Surveillance may include, for example, the drone 551 using a camera 551a to obtain 551b live video feeds or images that can be monitored by a security agent at a terminal provided access to the drone's 551 feed. The drone's 551 flight path 570 results in the drone coming up on property 511 first. The resident of property 511 either (i) has a user profile that permits the drone to fly through, and capture video surveillance of, the resident's property 511, or (ii) has not customized drone surveillance of his/her property. As a result, the drone 551 travels through the property's 511 airspace and obtains 551b video surveillance of the property 511.

Next, the drone's 551 flight path brings the drone within a predetermined threshold distance of the property 512 and the drone 551 accesses the resident of property's 512 user profile of customizable drone surveillance settings. Based on accessing the resident of property's 512 user profile of customizable drone surveillance settings, the drone 551 may determine that the resident of property 512 does not permit any drone surveillance within the property's 512 boundary line 512b. Accordingly, the drone's 551 flight path 570 is dynamically adjusted so that the drone 570 can continue onto the next property in the neighborhood to continue the drone's 551 neighborhood surveillance while staying clear of the boundary line 512b of property 512 per the resident of property's 512 customizable drone surveillance settings. Then, drone 551 may continue along its surveillance flight path 570 that takes the drone 551 through the airspace of property 513, property 514, and property 515, each of which are associated with resident user profiles that do not restrict the drone's surveillance of the respective properties at the time of the drone' 551 flight.

Next, the drone's 551 flight path 570 brings the drone 551 within a predetermined threshold distance of the property 516b where the drone 551 may access the property 516 resident's user profile. The property 516 resident's user profile may indicate that a drone 551 is not permitted within the boundary line 516b of the property 516 unless a security event notification or an emergency event notification has been generated by one or more sensors of the resident's property 516. In the example of FIG. 5, the drone 551 may determine that a glass break sensor and one or more motion sensors each generated a security event notification due to a potential home invasion by a burglar 560. Accordingly, the drone 551 may determine that the override condition established by property 516 resident's user profile is met that permits the drone to fly past the property's 516 boundary line 516b to engage the burglar 560.

Figure 6A:
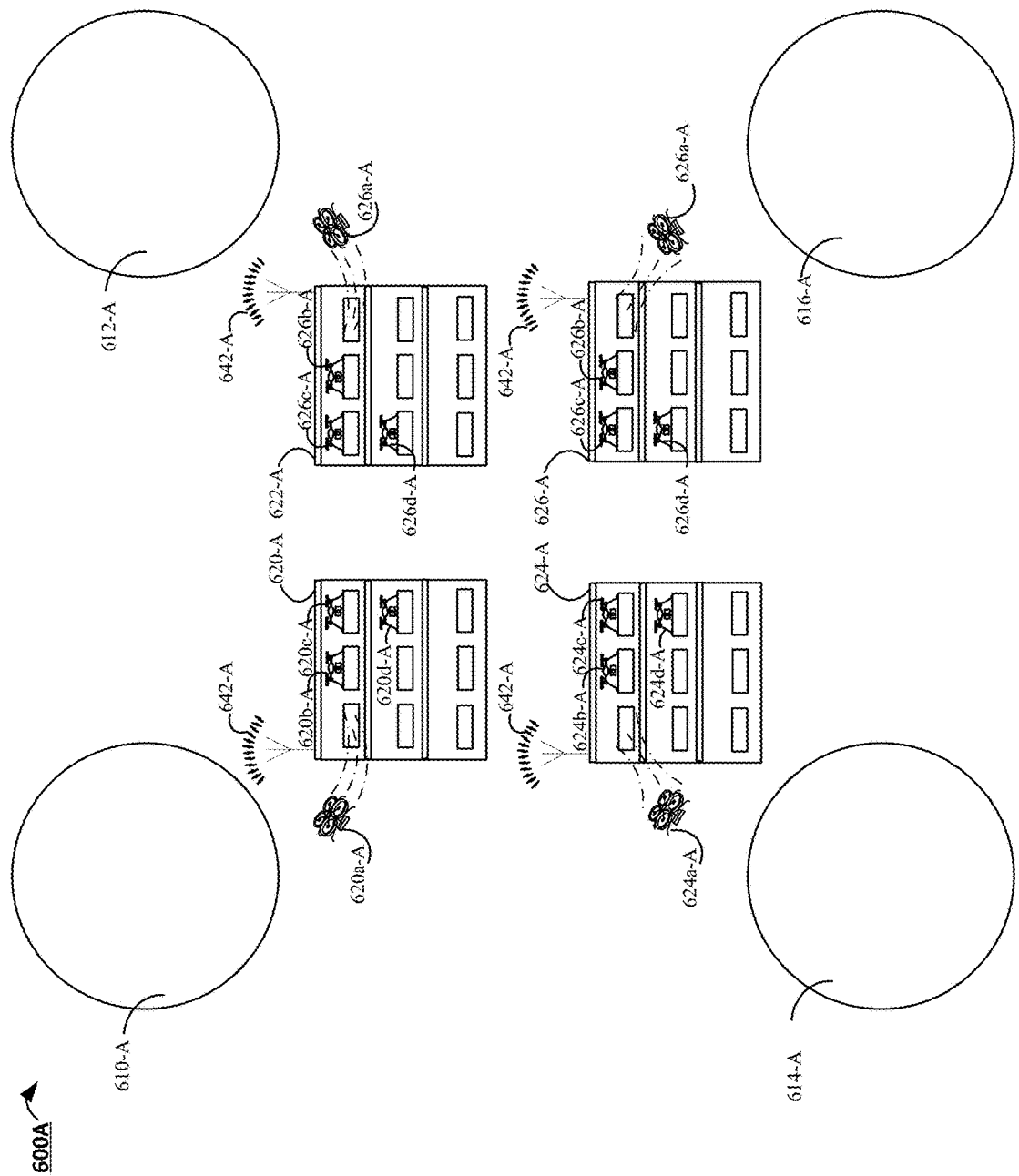
FIG. 6A is a contextual diagram of multiple drone base stations that house multiple drones for performing community-based drone augmented surveillance of multiple neighborhoods.

FIG. 6A is a contextual diagram of multiple drone base stations 620-A, 622-A, 624-A, 626-A that each house multiple drones for performing community-based drone augmented surveillance of multiple neighborhoods 610-A, 612-A, 614-A, 616-A.

Each drone base station 620-A, 622-A, 624-A, 626-A may be positioned outside of the respective neighborhood 610-A, 612-A, 614-A, 616-A to which the drone base station 620-A, 622-A, 624-A, 626-A provides drone surveillance and emergency services. Alternatively, or in addition, one or more drone base stations 620-A, 622-A, 624-A, 626-A may also reside within the neighborhood 610-A, 612-A, 614-A, 616-A to which the drone base station 620-A, 622-A, 624-A, 626-A provides drone surveillance and emergency services. In some implementations, a drone base station housing drones may be configured to provide community-based drone augmented surveillance to a particular neighborhood. For example, the drone base station 620-A may house a predetermined number of drones such as drones 620a-A, 620b-A, 620c-A, 620d-A that can be used to provide surveillance and emergency related assistance to the neighborhood 610-A. However, the present disclosure need not be so limited. For example, since each drone base station 620-A, 622-A, 624-A, 626-A is inherently limited to a predetermined number of drones that the particular drone base station can house, there may be instances where a first drone base station needs to request additional drones from a different drone base station. Accordingly, aspects of the subject matter disclosed by this specification provide for drone base station to drone base station communication to facilitate drone sharing.

Drone sharing may be particularly important during severe emergency events. This is because, of the predetermined number of drones housed by any particular drone base station, only a subset of the predetermined number of drones may be equipped to address a particular emergency such as, for example a fire. For example, assume a fire breaks out in neighborhood 610-A. In response to an instruction from a monitoring application server, the drone base station 620-A may deploy one or more drones equipped with water tanks/sprayers, sodium bicarbonate tanks/sprayers, or the like. However, if the fire persists for a long period of time or spreads (e.g., a wildfire in summer), the drone base station 620-A may either not have enough properly equipped drones to contain the fire or may run out of water tanks, sodium bicarbonate tanks, or the like needed to reinforce its firefighting drones. In such instances, the drone base station 620-A can request additional drone support from another drone base station such as drone base station 622-A, drone base station 624-A, or drone base station 626-A. Though drone base station 622-A, drone base station 624-A, or drone base station 626-A are each configured to primarily surveil neighborhood 612-A, neighborhood 614-A, and neighborhood 616-A, respectively, each of the drone base stations 622-A, 624-A, 626-A may deploy one or more drones to help fight the fires in neighborhood 610-A, if requested.

A monitoring station server associated with a first drone base station 620-A may monitor the first drone base station's supply of drones that are equipped to respond to each active security event, emergency event, or other alarm events in the neighborhood 610-A. For example, the monitoring station server associated with the first drone base station 620-A may determine whether the first drone base station's 620-A supply of drones equipped to respond to one or more of the active security events, emergency events, or other alarm events falls below a predetermined threshold. In response, the monitoring station server associated with the first drone base station 620-A may transmit a request for additional drones through a network using one or more communications links to another monitoring station server associated with a second drone base station 626-A. The request for additional drones may include a request for one or more drones having a particular capability that can be used to respond to, or otherwise address, the active security events, emergency events, or other alarm events that are ongoing in the neighborhood 610-A for which the first drone base station 620-A has a drone deficiency (e.g., a supply of drones to address the active security events, emergency events, or other alarm events that falls below a predetermined threshold). Alternatively, or in addition, the monitoring station server associated with the first drone base station 620-A may also send a general request for any additional drone having any capabilities to the other monitoring station server associated with the second drone base station 626-A.

In some instances, a drone deficiency may arise even if a first drone base station 620-A has a supply of drones that are equipped to address an active security event, emergency event, or other alarm event. For instance, though a first drone base station 620-A may have a supply of drones to address the active security event, emergency event, or other alarm event, the first drone base station's 620-A drones may not have a battery that is sufficiently charged due to extended deployments to respond to the active security event, emergency event, or other alarm event. Accordingly, when a monitoring station server associated with the first drone base station 620-A evaluates its current supply of drones equipped to address any particular security event, emergency event, or other alarm event, the monitoring station server associated with the first drone base station 620-A may not consider a drone with an insufficiently charged battery as a drone that is available for deployment to address an active security event, emergency event, or other alarm event. Similar exclusions of a drone from the first drone base station's available supply of drones may also be made if the drone is lacking a particular component necessary to perform its function (e.g., a fire fighting drone that has a fully charged battery but not water, sodium bicarbonate, or the like to fill its tank).

Figure 6B:
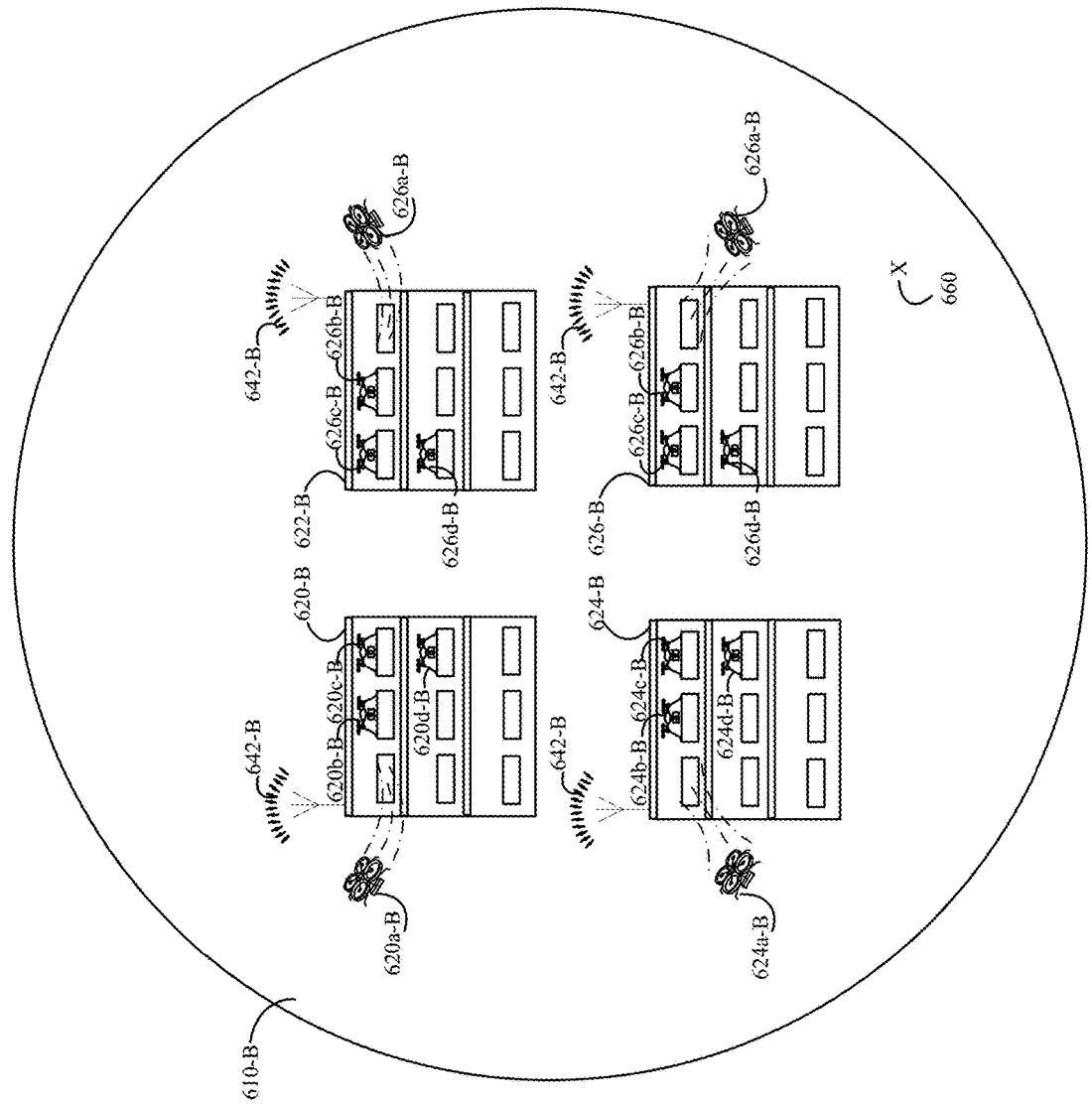
FIG. 6B is a contextual diagram of multiple drone base stations residing within a single neighborhood that house drones for performing community-based drone augmented surveillance of multiple neighborhoods.

FIG. 6B is a contextual diagram of multiple drone base stations residing within a single neighborhood 610B that each house drones for performing community-based drone augmented surveillance of a single neighborhood.

In some instances, one or more drone base stations may be located within a neighborhood. For example, drone base stations 620-B, 622-B, 624-B, 626-B may be located within a particular neighborhood such as neighborhood 610-B. Using drone base stations that are located within a neighborhood such as neighborhood such as neighborhood 610-B may provide for enhanced community-based drone augmented surveillance. The community-based augmented surveillance may be enhanced because drone response times, deployment times, or the like are reduced because the drones have a short distance to travel to any security events, emergency events, or other alarm events detected within the neighborhood 610-B because the drone base stations are located within the neighborhood 610-B.

Based on a detected security event, emergency event, or alarm event, a monitoring application server may instruct the drone base station 620-B, 622-B, 624-B, 626-B that is closest in proximity to the detected security event, emergency event, or alarm event to deploy one or more drones to investigate the detected event. For instance, assume that a monitoring application server receives a security event notification indicating that a security event is detected in at location 660. In such a scenario, the monitoring application server may transmit an instruction to the drone base station 626-B to deploy one or more drones 626a-B, 626b-B, 626c-B, 626d-B to the location 660 to investigate the security event 660.

In one implementation, the monitoring application server may transmit the instruction to monitoring station server that is assigned to manage deployment of the drones housed by the drone base station 626-B. Alternatively, the monitoring application server may configured to receiving alarm event notifications such as security event notifications, emergency event notifications, or the like and manage deployment of the drones housed by the drone base station 626-B without the assistance of a separate monitoring station server. In such instances, the monitoring application server may receive one or more alarm event notifications such as security event notification, emergency event notification, or the like and then transmit an instruction directly to one or more drones 626a-B, 626b-B, 626c-B, 626d-B to deploy to the location 660 associated with the alarm event notification.

Each of the drone base stations 620-B, 622-B, 624-B, 626-B residing within the neighborhood 610-B may share the drones that each respective drone base station houses with another drone base station in the same manner as described with respect to FIG. 6A. In some instances, the drone base stations 620-B, 622-B, 624-B, 626-B may be located at strategic locations throughout the neighborhood 610-B in an effort to reduce drone response times.

Though the example described with reference to FIG. 6B describes scenarios where a drone base station houses multiple drones 626a-B, 626b-B, 626c-B, 626d-B, the present disclosure need not be so limited. For instance, in one implementation, multiple different drone base stations may be distributed throughout the neighborhood 610-B that each house a single drone and a single charging station. By way of example, each drone base station may include a tall streetlight-esque structure that opens at the top to release the drone when the drone is deployed, or to receive the drone onto a charging station when a drone returns from deployment. Though drone base stations of multiple different sizes, shapes, and structures can be used, a tall streetlight-esque structure may prove beneficial to avoid members of the public from tampering with the drone maintained by each respective drone base station. In this scenario, drone base stations in the form of streetlight-esque structures may be arranged throughout a neighborhood 610-B. In some implementations, multiple drone base stations may be provided for each neighborhood street, block, or the like. In an implementation that utilizes drone base stations housing a small number of drones such as one drone, two drones, or the like, the community-based drone augmented surveillance system may be configured to operate without the aid of a dedicated monitoring station server. In such instances, a monitoring application server may function as both the monitoring application server and the monitoring station server. That is, the monitoring application server may receive security event notifications, emergency event notifications, or other alarm event notifications, and also manage deployment of the drones. In such an implementation, the monitoring application server may facilitate deployment of the drones by transmitting one or more deployment instructions directly to the drone housed by a respective base station, a processor associated with the drone base station, or a combination thereof.

Though a streetlight-esque structure is described above with reference to a drone base station, other structures may be used. For instance, short and squat structures similar in size and scope to a postal server drop box may be used to house a drone, charging station, and or the like on each street corner of a neighborhood. Alternatively, or in addition, one or more structures to house a drone, wireless charging station, or the like may be maintained underground, and be configured to rise up out of the ground on a platform when deployment of a drone is required (or similarly when a deployed drone arrives back from deployment). Yet other types of drone station structures may also be used.

Figure 7:
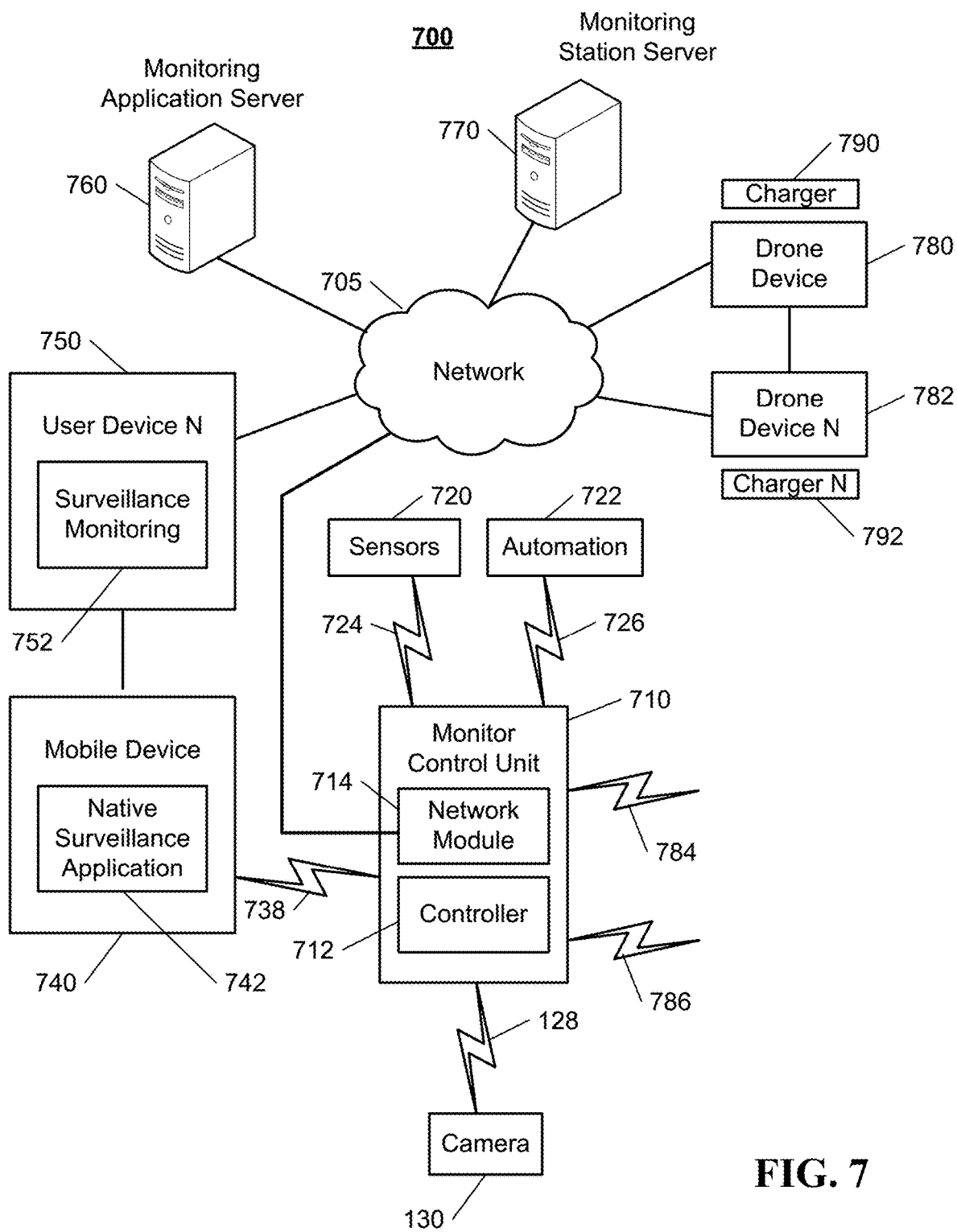
FIG. 7 is a block diagram of a surveillance system that utilizes one or more drones.

FIG. 7 is a block diagram of a surveillance system that utilizes one or more drones. The electronic system 700 includes a network 705, a monitor control unit 710, one or more user devices 740, 750, a monitoring application server 760, and a monitoring application server 760. In some implementations, the network 705 facilitates communications between the monitoring application server 760, and the monitoring station server 770.

The network 705 is configured to enable exchange of electronic communications between devices connected to the network 705. For example, the network 705 may be configured to enable exchange of electronic communications between the monitoring system control unit 710, the one or more user devices 740, 750, the monitoring application server 760, and the monitoring station server 770. The network 105 may include, for example, one or more of the Internet, Wide Area Networks (WANs), Local Area Networks (LANs), analog or digital wired and wireless telephone networks (e.g., a public switched telephone network (PSTN), Integrated Services Digital Network (ISDN), a cellular network, and Digital Subscriber Line (DSL)), radio, television, cable, satellite, or any other delivery or tunneling mechanism for carrying data. Network 705 may include multiple networks or subnetworks, each of which may include, for example, a wired or wireless data pathway. The network 705 may include a circuit-switched network, a packet-switched data network, or any other network able to carry electronic communications (e.g., data or voice communications). For example, the network 705 may include networks based on the Internet protocol (IP), asynchronous transfer mode (ATM), the PSTN, packet-switched networks based on IP, X.25, or Frame Relay, or other comparable technologies and may support voice using, for example, VoIP, or other comparable protocols used for voice communications. The network 705 may include one or more networks that include wireless data channels and wireless voice channels. The network 705 may be a wireless network, a broadband network, or a combination of networks including a wireless network and a broadband network.

The monitoring system control unit 710 includes a controller 712 and a network module 714. The controller 712 is configured to control a monitoring system (e.g., a home alarm or security system) that includes the monitoring system control unit 710. In some implementations, the controller 712 may include a processor or other control circuitry configured to execute instructions of a program that controls operation of an alarm system. In these examples, the controller 712 may be configured to receive input from sensors, detectors, or other devices included in the alarm system and control operations of devices included in the alarm system or other household devices (e.g., a thermostat, an appliance, lights, etc.). For example, the controller 712 may be configured to control operation of the network module 714 included in the monitoring system control unit 710.

The network module 714 is a communication device configured to exchange communications over the network 705. The network module 714 may be a wireless communication module configured to exchange wireless communications over the network 705. For example, the network module 714 may be a wireless communication device configured to exchange communications over a wireless data channel and a wireless voice channel. In this example, the network module 714 may transmit alarm data over a wireless data channel and establish a two-way voice communication session over a wireless voice channel. The wireless communication device may include one or more of a LTE module, a GSM module, a radio modem, cellular transmission module, or any type of module configured to exchange communications in one of the following formats: LTE, GSM or GPRS, CDMA, EDGE or EGPRS, EV-DO or EVDO, UMTS, or IP.

The network module 714 also may be a wired communication module configured to exchange communications over the network 705 using a wired connection. For instance, the network module 714 may be a modem, a network interface card, or another type of network interface device. The network module 714 may be an Ethernet network card configured to enable the monitoring system control unit 710 to communicate over a local area network and/or the Internet. The network module 714 also may be a voiceband modem configured to enable the alarm panel to communicate over the telephone lines of Plain Old Telephone Systems (POTS).

The monitoring system that includes the monitoring system control unit 710 includes one or more sensors or detectors. For example, the monitoring system may include multiple sensors 720. The sensors 720 may include a contact sensor, a motion sensor, a glass break sensor, or any other type of sensor included in an alarm system or security system. The sensors 720 also may include an environmental sensor, such as a temperature sensor, a water sensor, a rain sensor, a wind sensor, a light sensor, a smoke detector, a carbon monoxide detector, an air quality sensor, etc. The sensors 720 further may include a health monitoring sensor, such as a prescription bottle sensor that monitors taking of prescriptions, a blood pressure sensor, a blood sugar sensor, a bed mat configured to sense presence of liquid (e.g., bodily fluids) on the bed mat, etc. In some implementations, the sensors 720 may include a radio-frequency identification (RFID) sensor that identifies a particular article that includes a pre-assigned RFID tag.

The monitoring system control unit 710 communicates with the module 722 and the camera 730 to perform surveillance or monitoring. The module 722 is connected to one or more devices that enable home automation control. For instance, the module 722 may be connected to one or more lighting systems and may be configured to control operation of the one or more lighting systems. Also, the module 722 may be connected to one or more electronic locks at the property and may be configured to control operation of the one or more electronic locks (e.g., control Z-Wave locks using wireless communications in the Z-Wave protocol). Further, the module 722 may be connected to one or more appliances at the property and may be configured to control operation of the one or more appliances. The module 722 may include multiple modules that are each specific to the type of device being controlled in an automated manner. The module 722 may control the one or more devices based on commands received from the monitoring system control unit 710. For instance, the module 722 may cause a lighting system to illuminate an area to provide a better image of the area when captured by a camera 730.

The camera 730 may be a video/photographic camera or other type of optical sensing device configured to capture images. For instance, the camera 730 may be configured to capture images of an area within a building monitored by the monitoring system control unit 710. The camera 730 may be configured to capture single, static images of the area and also video images of the area in which multiple images of the area are captured at a relatively high frequency (e.g., thirty images per second). The camera 730 may be controlled based on commands received from the monitoring system control unit 710.

The camera 730 may be triggered by several different types of techniques. For instance, a Passive Infra Red (PIR) motion sensor may be built into the camera 730 and used to trigger the camera 730 to capture one or more images when motion is detected. The camera 730 also may include a microwave motion sensor built into the camera and used to trigger the camera 730 to capture one or more images when motion is detected. The camera 730 may have a "normally open" or "normally closed" digital input that can trigger capture of one or more images when external sensors (e.g., the sensors 720, PIR, door/window, etc.) detect motion or other events. In some implementations, the camera 730 receives a command to capture an image when external devices detect motion or another potential alarm event. The camera 730 may receive the command from the controller 712 or directly from one of the sensors 720.

In some implementations, the camera 730 triggers integrated or external illuminators (e.g., Infra Red, Z-wave controlled "white" lights, lights controlled by the module 722, etc.) to improve image quality when the scene is dark. An integrated or separate light sensor may be used to determine if illumination is desired and may result in increased image quality.

The camera 730 may be programmed with any combination of time/day schedules, system "arming state", or other variables to determine whether images should be captured or not when triggers occur. The camera 730 may enter a low-power mode when not capturing images. In this case, the camera 730 may wake periodically to check for inbound messages from the controller 712. The camera 730 may be powered by internal, replaceable batteries if located remotely from the monitoring control unit 710. The camera 730 may employ a small solar cell to recharge the battery when light is available. Alternatively, the camera 730 may be powered by the controller's 712 power supply if the camera 730 is co-located with the controller 712.

In some implementations, the camera 730 communicates directly with the monitoring application server 760 over the Internet. In these implementations, image data captured by the camera 730 does not pass through the monitoring system control unit 710 and the camera 730 receives commands related to operation from the monitoring application server 760.

The system 700 further includes one or more drone devices 780 and 782. The drone devices 780 and 782 may be unmanned devices that are capable of movement. For example, the drone devices 780 and 782 may be capable of moving throughout a location based on automated control technology and/or user input control provided by either the user or by application server 760. In such an example, the drone devices 780 and 782 may be able to fly, roll, walk, or otherwise move about a location. The drone devices 780 and 782 may include helicopter type devices (e.g., quad copters), rolling helicopter type devices (e.g., roller copter devices that can fly and also roll along the grounds, walls, or ceiling), land vehicle type devices (e.g., automated cars that drive around a property), and plane type devices (e.g., unmanned aircraft). In some instances, the drone devices 780 and 782 may be drone devices that are intended for other purposes and merely associated with the monitoring system 700 for use in appropriate circumstances. For instance, a security drone may be associated with the monitoring system 700 as one of the drone devices 780 and 782 and may be controlled to take action responsive to monitoring system events.

In some implementations, the drone devices 780 and 782 automatically navigate to a location of a property in response to receiving an alarm signal from the monitoring application server 760. In these examples, the drone devices 780 and 782 include sensors and control processors that guide movement of the drone devices 780 and 782 to the location of the property. For instance, the drone devices 780 and 782 may navigate to the location using one or more cameras, one or more proximity sensors, one or more gyroscopes, one or more accelerometers, one or more magnetometers, a global positioning system (GPS) unit, an altimeter, one or more sonar or laser sensors, and/or any other types of sensors that aid in navigation about the location. The drone devices 780 and 782 may include control processors that process output from the various sensors and control the drone devices 780 and 782 to move along a path that reaches the desired destination and avoids obstacles. In this regard, the control processors detect obstructions and guide movement of the drone devices 780 and 782 in a manner that avoids the obstructions.

In addition, the drone devices 780 and 782 may store data that describes attributes of the property. For instance, the drone devices 780 and 782 may store a three-dimensional exterior model of the property that enables the drone devices 780 and 782 to navigate outside the property. During initial configuration, the drone devices 780 and 782 may receive the data describing attributes of the property, determine a frame of reference to the data (e.g., a home or reference location in the property), and navigate the property location based on the frame of reference and the data describing attributes of the property. Further, initial configuration of the drone devices 780 and 782 also may include learning of one or more navigation patterns in which a user provides input to control the drone devices 780 and 782 to perform a specific navigation action (e.g., fly to the property location and spin around while capturing video and then return to a monitoring station). In this regard, the drone devices 780 and 782 may learn and store the navigation patterns such that the drone devices 780 and 782 may automatically repeat the specific navigation actions upon a later request.

In some implementations, the drone devices 780 and 782 may include data capture and recording devices. In these examples, the drone devices 780 and 782 may include one or more cameras, one or more motion sensors, one or more microphones, one or more biometric data collection tools, one or more temperature sensors, one or more humidity sensors, one or more air flow sensors, and/or any other types of sensors that may be useful in capturing monitoring data related to the property location.

In some implementations, the drone devices 780 and 782 may include output devices. In these implementations, the drone devices 780 and 782 may include one or more displays, one or more speakers, one or more projectors, and/or any type of output devices that allow the drone devices 780 and 782 to communicate information to a nearby user. The one or more projectors may include projectors that project a two-dimensional image onto a surface (e.g., wall, floor, or ceiling) and/or holographic projectors that project three-dimensional holograms into a nearby space.

The drone devices 780 and 782 also may include a communication module that enables the drone devices 780 and 782 to communicate with the monitoring application server 760, each other, and/or other devices. The communication module may be a wireless communication module that allows the drone devices 780 and 782 to communicate wirelessly. For instance, the communication module may be a Wi-Fi module that enables the drone devices 780 and 782 to communicate over a local wireless network at the property. The communication module further may be a 900 MHz wireless communication module that enables the drone devices 780 and 782 to communicate directly with the monitoring application server 760. Other types of short-range wireless communication protocols, such as Bluetooth, Bluetooth LE, Zwave, Zigbee, etc., may be used to allow the drone devices 780 and 782 to communicate with other devices in the property.

The drone devices 780 and 782 further may include processor and storage capabilities. The drone devices 780 and 782 may include any suitable processing devices that enable the drone devices 780 and 782 to operate applications and perform the actions described throughout this disclosure. In addition, the drone devices 780 and 782 may include solid state electronic storage that enables the drone devices 780 and 782 to store applications, configuration data, collected sensor data, and/or any other type of information available to the drone devices 780 and 782.

The drone devices 780 and 782 are associated with one or more charging stations 790 and 792. The charging stations 790 and 792 may be centrally located at predefined base or reference locations near a neighborhood that includes multiple properties. For example, in some instances, the one or more charging stations 790 and 792 may be located on a central monitoring station where the monitoring application server 760 may be located. In other examples, the one or more charging stations 790 and 792 may be located in a monitoring station that is in a different location than the monitoring application server 760. In some implementations, the charging station may be mobile, deployable to a particular location, or the like. For instance, if drones are deployed to a particular location, one or more charging station may be deployed to the same location. The deployed charging stations can be powered from the electrical grid, be solar powered, attached to propane gasoline hookups, attached to natural gas hookups, or the like.

The drone devices 780 and 782 may be configured to navigate to the charging stations 790 and 792 after completion of tasks needed to be performed for the monitoring system 700. For instance, after completion of a monitoring operation at a particular property location, or upon instruction by the monitoring application server 760, the drone devices 780 and 782 may be configured to automatically fly to and land on one of the charging stations 790 and 792. In this regard, the drone devices 780 and 782 may automatically maintain a fully charged battery in a state in which the drone devices 780 and 782 are ready for use by the monitoring system 700.

The charging stations 790 and 792 may be contact based charging stations and/or wireless charging stations. For contact based charging stations, the drone devices 780 and 782 may have readily accessible points of contact that the drone devices 780 and 782 are capable of positioning and mating with a corresponding contact on the charging station. For instance, a helicopter type drone device may have an electronic contact on a portion of its landing gear that rests on and mates with an electronic pad of a charging station when the helicopter type drone device lands on the charging station. The electronic contact on the drone device may include a cover that opens to expose the electronic contact when the drone device is charging and closes to cover and insulate the electronic contact when the drone device is in operation.

For wireless charging stations, the drone devices 780 and 782 may charge through a wireless exchange of power. In these cases, the drone devices 780 and 782 need only locate themselves closely enough to the wireless charging stations for the wireless exchange of power to occur. In this regard, the positioning needed to land at a predefined home base or reference location in the property may be less precise than with a contact based charging station. Based on the drone devices 780 and 782 landing at a wireless charging station, the wireless charging station outputs a wireless signal that the drone devices 780 and 782 receive and convert to a power signal that charges a battery maintained on the drone devices 780 and 782.

In some implementations, the drone devices 780 and 782 may additionally be used to perform routine surveillance operations on a property location. For instance, the drone devices 780 and 782 may be assigned to one or more particular properties within a geographic location and may routinely collect surveillance footage during specified time periods (e.g., after dark), which may then be transmitted to the monitoring application server 760 for transmitting back to each particular property owner. In such implementations, the property owner may receive the surveillance footage over the network 705 as a part of a service provided by a security provider that operates the monitoring application server 760. For example, transmissions of the surveillance footage collected by the drone devices 780 and 782 may be part of a premium security service package provided by a security provider in addition to the routine drone emergency response service.

In some implementations, each of the drone devices 780 and 782 has a corresponding and assigned charging station 790 and 792 such that the number of drone devices 780 and 782 equals the number of charging stations 790 and 792. In these implementations, the drone devices 780 and 782 always navigate to the specific charging station assigned to that drone device. For instance, the drone device 780 may always use changing station 790 and the drone device 782 may always use changing station 792.

In some implementations, the drone devices 780 and 782 may share charging stations. For instance, the drone devices 780 and 782 may use one or more community charging stations that are capable of charging multiple drone devices 780 and 782. The community charging station may be configured to charge multiple drone devices 780 and 782 in parallel. The community charging station may be configured to charge multiple drone devices 780 and 782 in serial such that the multiple drone devices 780 and 782 take turns charging and, when fully charged, return to a predefined home base or reference location in the property that is not associated with a charger. The number of community charging stations may be less than the number of drone devices 780 and 782.

The charging stations 790 and 792 may be co-housed or placed nearby locations where alarm stations for properties may be located. For example, in some instances, the charging stations 790 and 792 may be placed within a particular location near a property such that the drone devices 780 and 782 may respond to an alarm signal generated by the alarm system of the property. In other instances, the charging stations 790 and 792 may be placed in particular locations within a community and configured to store drone devices 780 and 782 that service multiple properties within the community. For example, the charging stations 790 and 792 may be placed near elevated regions within a community such that the drone devices 780 and 782 may descend to a particular location within the community in response to an alarm event at the particular location within the community.

In some implementations, the charging stations 790 and 792 may additionally include solar panels to charge the drone devices 780 and 782 to conserve energy needed to charge the drone devices 780 and 782. In such implementations, the charging stations 790 and 792 may include controllers that are capable in adjusting the power source to the drone devices 780 and 782 to modulate charging speeds. For example, the charging stations 790 and 792 may use a high energy power source to charge the drone devices 780 and 782 at high speeds in anticipation of high volume of alarm events, and use a low energy power source to charge the drone devices 780 and 782 at low speeds during times when there is a low volume of alarm events (e.g., during times of low user activity).

Also, the charging stations 790 and 792 may not be assigned to specific drone devices 780 and 782 and may be capable of charging any of the drone devices 780 and 782. In this regard, the drone devices 780 and 782 may use any suitable, unoccupied charging station when not in use. For instance, when one of the drone devices 780 and 782 has completed an operation or is in need of battery charge, the monitoring system control unit 710 references a stored table of the occupancy status of each charging station and instructs the drone device to navigate to the nearest charging station that is unoccupied.

The sensors 720, the module 722, the camera 730, and the drone devices 780 and 782 communicate with the controller 712 over communication links 724, 726, and 728. The communication links 724, 726, and 728 may be a wired or wireless data pathway configured to transmit signals from the sensors 720, the module 722, the camera 730, and the drone devices 780 and 782 to the controller 712. The sensors 720, the module 722, the camera 730, and the drone devices 780 and 782 may continuously transmit sensed values to the controller 712, periodically transmit sensed values to the controller 712, or transmit sensed values to the controller 712 in response to a change in a sensed value.

The communication links 724, 726, and 728 may include a local network. The sensors 720, the module 722, the camera 730, and the drone devices 780 and 782 and the controller 712 may exchange data and commands over the local network. The local network may include 802.11 "WiFi" wireless Ethernet (e.g., using low-power WiFi chipsets), Z-Wave, Zigbee, Bluetooth, "Homeplug" or other "Powerline" networks that operate over AC wiring, and a Category 5 (CAT5) or Category 6 (CAT6) wired Ethernet network. The local network may be a mesh network constructed based on the devices connected to the mesh network.

The monitoring application server 760 is an electronic device configured to provide alarm monitoring service by exchanging communications with the monitoring system control unit 710, the one or more mobile devices 740, 750, and the monitoring application server 760 over the network 705. For example, the monitoring application server 760 may be configured to monitor alarm events generated by the monitoring system control unit 710. In this example, the monitoring application server 760 may exchange communications with the network module 714 included in the monitoring system control unit 710 to receive information regarding alarm events detected by the monitoring system control unit 710. The monitoring application server 760 also may receive information regarding alarm events from the one or more mobile devices 740, 750 and/or the monitoring station server 770.

In some implementations, the monitoring application server 760 may route alarm data received from the network module 714 or the one or more user devices 740, 750 to the monitoring station server 770. For example, the monitoring application server 760 may transmit the alarm data to the monitoring station server 770 over the network 705.

The monitoring application server 760 may store sensor and image data received from the monitoring system and perform analysis of sensor and image data received from the monitoring system. Based on the analysis, the monitoring application server 760 may communicate with and control aspects of the monitoring system control unit 710 or the one or more user devices 740, 750.

The monitoring application server 760 is connected to multiple terminals. The terminals may be used by operators to process alarm events. For example, the monitoring application server 760 may route alarm data to the terminals to enable an operator to process the alarm data. The terminals may include general-purpose computers (e.g., desktop personal computers, workstations, or laptop computers) that are configured to receive alarm data from a server in the monitoring application server 760 and render a display of information based on the alarm data. For instance, the controller 712 may control the network module 714 to transmit, to the monitoring application server 760, alarm data indicating that a sensor 720 detected a door opening when the monitoring system was armed. The monitoring application server 760 may receive the alarm data and route the alarm data to the terminal for processing by an operator associated with the terminal. The terminal may render a display to the operator that includes information associated with the alarm event (e.g., the name of the user of the alarm system, the address of the building the alarm system is monitoring, the type of alarm event, etc.) and the operator may handle the alarm event based on the displayed information.

In some implementations, the terminals may be mobile devices or devices designed for a specific function. Although FIG. 7 illustrates two terminals for brevity, actual implementations may include more (and, perhaps, many more) terminals.

In some implementations, the monitoring application server 760 may exchange communications with an emergency service provider to transmit alarm signal data indicating an alarm event taking place within a property where the monitor control unit 710 may be located. For instance, the monitoring application server 760 may transmit incident reports in response to the monitor control unit 710 detecting an alarm event where a user requires emergency assistance. In such instances, the monitoring application server 760 may be an electronic device that communicates essential safety information to an emergency responder such as an emergency medial responder, a fire department, or a public safety access point.

In some implementations, the monitoring application server 760 may be a third party entity separate from the monitoring station server 760. For example, the monitoring application server 760 may be a central alarm station for a security service provider, a campus security server in a school or school/university police department, or security gateway for a particular residential neighborhood. For instance, the monitoring application server 760 may be registered to the system 700 using a connection bridge such as the application (e.g., the native surveillance application 742), using a unique user identifier such as a username and password or a Quick Response (QR). In other instances, the monitoring application server 760 may be registered to users within a particular geographic location (e.g., a gated residential community) where users within the geographical location are registered to a particular monitoring application server 760 and a particular monitoring station server 770 of the particular location.

The one or more user devices 740, 750 are devices that host and display user interfaces. For instance, the user device 740 is a mobile device that hosts one or more native applications (e.g., the native surveillance application 742). The user device 740 may be a cellular phone or a non-cellular locally networked device with a display. The user device 740 may include a cell phone, a smart phone, a tablet PC, a personal digital assistant ("PDA"), or any other portable device configured to communicate over a network and display information. For example, implementations may also include Blackberry-type devices (e.g., as provided by Research in Motion), electronic organizers, iPhone-type devices (e.g., as provided by Apple), iPod devices (e.g., as provided by Apple) or other portable music players, other communication devices, and handheld or portable electronic devices for gaming, communications, and/or data organization. The user device 740 may perform functions unrelated to the monitoring system, such as placing personal telephone calls, playing music, playing video, displaying pictures, browsing the Internet, maintaining an electronic calendar, etc.

The user device 740 includes a native surveillance application 742. The native surveillance application 742 refers to a software/firmware program running on the corresponding mobile device that enables the user interface and features described throughout. The user device 740 may load or install the native surveillance application 742 based on data received over a network or data received from local media. The native surveillance application 742 runs on mobile devices platforms, such as iPhone, iPod touch, Blackberry, Google Android, Windows Mobile, etc. The native surveillance application 742 enables the user device 740 to receive and process image and sensor data from the monitoring system.

The user device 750 may be a general-purpose computer (e.g., a desktop personal computer, a workstation, or a laptop computer) that is configured to communicate with the monitoring application server 760 and/or the monitoring system control unit 710 over the network 705. The user device 750 may be configured to display a surveillance monitoring user interface 752 that is generated by the user device 750 or generated by the monitoring application server 760. For example, the user device 750 may be configured to display a user interface (e.g., a web page) provided by the monitoring application server 760 that enables a user to perceive images captured by the camera 730 and/or reports related to the monitoring system. Although FIG. 7 illustrates two user devices for brevity, actual implementations may include more (and, perhaps, many more) or fewer user devices.

In some implementations, the one or more user devices 740, 750 communicate with and receive monitoring system data from the monitoring system control unit 710 using the communication link 738. For instance, the one or more user devices 740, 750 may communicate with the monitoring system control unit 710 using various local wireless protocols such as wife, Bluetooth, zwave, zigbee, HomePlug (ethernet over powerline), or wired protocols such as Ethernet and USB, to connect the one or more user devices 740, 750 to local security and automation equipment. The one or more user devices 740, 750 may connect locally to the monitoring system and its sensors and other devices. The local connection may improve the speed of status and control communications because communicating through the network 105 with a remote server (e.g., the monitoring application server 760) may be significantly slower.

Although the one or more user devices 740, 750 are shown as communicating with the monitoring system control unit 710, the one or more user devices 740, 750 may communicate directly with the sensors and other devices controlled by the monitoring system control unit 710. In some implementations, the one or more user devices 740, 750 replace the monitoring system control unit 710 and perform the functions of the monitoring system control unit 710 for local monitoring and long range/offsite communication.

In other implementations, the one or more user devices 740, 750 receive monitoring system data captured by the monitoring system control unit 710 through the network 705. The one or more user devices 740, 750 may receive the data from the monitoring system control unit 710 through the network 705 or the monitoring application server 760 may relay data received from the monitoring system control unit 710 to the one or more user devices 740, 750 through the network 705. In this regard, the monitoring application server 760 may facilitate communication between the one or more user devices 740, 750 and the monitoring system.

In some implementations, the one or more user devices 740, 750 may be configured to switch whether the one or more user devices 740, 750 communicate with the monitoring system control unit 710 directly (e.g., through link 738) or through the monitoring application server 760 (e.g., through network 705) based on a location of the one or more user devices 740, 750. For instance, when the one or more user devices 740, 750 are located close to the monitoring system control unit 710 and in range to communicate directly with the monitoring system control unit 710, the one or more user devices 740, 750 use direct communication. When the one or more user devices 740, 750 are located far from the monitoring system control unit 710 and not in range to communicate directly with the monitoring system control unit 710, the one or more user devices 740, 750 use communication through the monitoring application server 760.

Although the one or more user devices 740, 750 are shown as being connected to the network 105, in some implementations, the one or more user devices 740, 750 are not connected to the network 705. In these implementations, the one or more user devices 740, 750 communicate directly with one or more of the monitoring system components and no network (e.g., Internet) connection or reliance on remote servers is needed.

In some implementations, the one or more user devices 740, 750 are used in conjunction with only local sensors and/or local devices in a house. In these implementations, the system 700 only includes the one or more user devices 740, 750, the sensors 720, the module 722, the camera 730, and the drone devices 780 and 782. The one or more user devices 740, 750 receive data directly from the sensors 720, the module 722, the camera 730, and the drone devices 780 and 782 and sends data directly to the sensors 720, the module 722, the camera 730, and the drone devices 780 and 782. The one or more user devices 740, 750 provide the appropriate interfaces/processing to provide visual surveillance and reporting.

In other implementations, the system 700 further includes network 705 and the sensors 720, the module 722, the camera 730, and the drone devices 780 and 782 are configured to communicate sensor and image data to the one or more user devices 740, 750 over network 705 (e.g., the Internet, cellular network, etc.). In yet another implementation, the sensors 720, the module 722, the camera 730, and the drone devices 780 and 782 (or a component, such as a bridge/router) are intelligent enough to change the communication pathway from a direct local pathway when the one or more user devices 740, 750 are in close physical proximity to the sensors 720, the module 722, the camera 730, and the drone devices 780 and 782 to a pathway over network 705 when the one or more user devices 740, 750 are farther from the sensors 720, the module 722, the camera 730, and the drone devices 780 and 782. In some implementations, the system leverages GPS information from the one or more user devices 740, 750 to determine whether the one or more user devices 740, 750 are close enough to the sensors 720, the module 722, the camera 730, and the drone devices 780 and 782 to use the direct local pathway or whether the one or more user devices 740, 750 are far enough from the sensors 720, the module 722, the camera 730, and the drone devices 780 and 782 that the pathway over network 705 is required. In other examples, the system leverages status communications (e.g., pinging) between the one or more user devices 740, 750 and the sensors 720, the module 722, the camera 730, and the drone devices 780 and 782 to determine whether communication using the direct local pathway is possible. If communication using the direct local pathway is possible, the one or more user devices 740, 750 communicate with the sensors 720, the module 722, the camera 730, and the drone devices 780 and 782 using the direct local pathway. If communication using the direct local pathway is not possible, the one or more user devices 740, 750 communicate with the sensors 720, the module 722, the camera 730, and the drone devices 780 and 782 using the pathway over network 705.

In some implementations, the system 700 provides end users with access to images captured by the camera 730 to aid in decision making. The system 700 may transmit the images captured by the camera 730 over a wireless WAN network to the user devices 740, 750. Because transmission over a wireless WAN network may be relatively expensive, the system 700 uses several techniques to reduce costs while providing access to significant levels of useful visual information.

In some implementations, a state of the monitoring system and other events sensed by the monitoring system may be used to enable/disable video/image recording devices (e.g., the camera 730). In these implementations, the camera 730 may be set to capture images on a periodic basis when the alarm system is armed in an "Away" state, but set not to capture images when the alarm system is armed in a "Stay" state or disarmed. In addition, the camera 730 may be triggered to begin capturing images when the alarm system detects an event, such as an alarm event, a door opening event for a door that leads to an area within a field of view of the camera 730, or motion in the area within the field of view of the camera 730. In other implementations, the camera 130 may capture images continuously, but the captured images may be stored or transmitted over a network when needed.

Further, in some implementations, the system 700 intelligently leverages the drone devices 780 and 782 to aid in security monitoring, property automation, and property management. For example, the drone devices 780 and 782 may aid in investigating alarm events detected at the property by the monitoring system control unit 710. In this example, the monitoring system control unit 710 may detect an alarm event (e.g., a fire alarm, an entry into the property when the system is armed "Stay," etc.) and, based on the detected alarm event, control the drone devices 780 and 782 to attempt to identify persons in the property at the time of the alarm event. Specifically, the monitoring application server 760 may send a control command to each of the drone devices 780 and 782 that causes the drone devices 780 and 782 to perform a coordinated and automated search for persons outside the property. Based on the control command received, each of the drone devices 780 and 782 begins navigating towards the property and captures images of the property while navigating. Each of the drone devices 780 and 782 may execute a predefined navigation pattern outside the property or the drone devices 780 and 782 may execute a coordinated scan of the property in which the drone devices 780 and 782 exchange location information and navigate to areas that have not been explored by one of the other devices.

In some implementations, the drone devices 780 and 782 may analyze the images captured during the scan of the property for the presence of persons in the captured images. For instance, the drone devices 780 and 782 may use image processing techniques in an attempt to identify shapes in the captured images that resemble a human body. The drone devices 780 and 782 also may analyze the images for moving objects (or use other techniques to identify moving objects) and target imaging on capture of moving objects.

Based on detection of a human or a moving object, the drone devices 780 and 782 may lock onto the human or moving object and follow the human or moving object throughout the property. In this regard, the drone devices 780 and 782 may follow the human or moving object throughout the property and capture images of the movement. In addition, once one of the drone devices 780 and 782 locks onto a human or moving object, the drone devices 780 and 782 coordinate to ensure that multiple of the drone devices 780 and 782 do not lock onto the same human or moving object. The coordination may be direct amongst the drone devices 780 and 782 and/or through the monitoring system control unit 710. The coordination may involve sharing the location of the human or moving object and/or attributes of the human or moving object being imaged. Based on the shared location and attributes, the drone devices 780 and 782 may determine whether multiple drone devices 780 and 782 have locked onto the same object and take action accordingly. If the drone devices 780 and 782 determine that the drone devices 780 and 782 have not locked onto the same object, the appropriate one of the drone devices 780 and 782 continues to lock onto the object while the other drone devices scan other areas of the property for other objects. If the drone devices 780 and 782 determine that the drone devices 780 and 782 have locked onto the same object, the drone devices 780 and 782 negotiate to determine which of the drone devices 780 and 782 will continue to lock onto the object while the other drone devices stop locking onto the object and scan other areas of the property for other objects. The negotiation may select the drone device that continues tracking the object based on one or more factors including the timing of when the devices locked onto the object (e.g., which device locked onto the object first), the positioning of the devices relative to the object (e.g., which is best positioned to image the object), the amount of battery power remaining (e.g., the device with the most battery power remaining), or any other factor that indicates the device most suited to track the object. To the extent the device tracking an object becomes less suitable for tracking the object (e.g., the battery power is running low), the drone devices 780 and 782 may coordinate to hand off tracking of the object to another one of the drone devices 780 and 782.

In some implementations, the drone devices 780 and 782 perform image recognition processing on the one or more images in an attempt to detect whether any identified humans are legitimate users of the property or intruders. In these examples, the drone devices 780 and 782 may have access to images of legitimate users of the property and may compare images being captured to the accessed images of legitimate users. Based on the comparison, the drone devices 780 and 782 use facial recognition techniques to determine whether the imaged user matches a legitimate user of the property or an intruder. The drone devices 780 and 782 then use the determination of whether the imaged user matches a legitimate user of the property or an intruder to control further tracking operation.

For example, based on a determination that the imaged user is an intruder, the drone devices 780 and 782 may continue tracking the intruder and ensure that images sufficient to identify the intruder have been captured. In this example, the drone devices 780 and 782 may attempt to capture biometric data from the intruder, such as voiceprint data, fingerprint data, and/or biological samples with DNA of the intruder. In addition, the drone devices 780 and 782 may take action to thwart the purpose of the intruder. For example, the drone devices 780 and 782 may fly in random patterns around the intruder, may play loud sounds near the intruder, may shine lights near the intruder, may output identifying information collected about the intruder (e.g., male, around six feet tall and one hundred eighty pounds), may enable a drone base station operator or first responder to talk to the intruder through a two-way voice communication session established through the monitoring system control unit 710 and the drone device, and may take other actions directed to disrupting the intruder.

Alternatively, based on a determination that the imaged user is a legitimate user, the drone devices 780 and 782 may discontinue tracking the legitimate user and scan for intruders. The drone devices 780 and 782 also may report the location of the legitimate user. The drone devices 780 and 782 further may continue tracking the legitimate user and attempt to provide assistance to the user. For instance, if the alarm is a fire alarm event, the drone devices 780 and 782 may stay near the legitimate user, continuously or periodically update the location of the legitimate user to assist another user or first responder in helping the legitimate user, provide audible reminders of what types of actions should be taken in a fire, enable a drone base station operator or first responder to talk to the legitimate user through a two-way voice communication session established through the monitoring system control unit 710 and the drone device, and may take other actions directed to assisting the legitimate user.

In some implementations, the drone devices 780 and 782 may be assigned to different areas of the property where the drone devices 780 and 782 can move in an unobstructed manner. In these examples, the drone devices 780 and 782 may be assigned to different levels in a property (e.g., an upstairs drone device and a downstairs drone device) and even different rooms or sections that are potentially blocked by doors. The monitoring system control unit 710 coordinate tracking movement based on the assigned areas. For instance, the monitoring system control unit 710 determines areas in a property where an event has been detected (e.g., where motion is sensed, where a door or window is opened, etc.) and only controls the drone devices assigned to the determined areas to operate. In this regard, the monitoring system control unit 710 may use location of users determined using sensors to control operation of the drone devices 780 and 782.

In some implementations, the monitoring application server 760 may monitor operational status of the drone devices 780 and 782 and coordinate further operation based on the operational status. In these implementations, the monitoring application server 760 may detect that a particular drone device is no longer operational and control one or more other drone devices to perform operations originally assigned to the non-operational drone device. In addition, the monitoring application server 760 may determine that the non-operational drone device was navigating close to an intruder and received an impact based on accelerometer data prior to becoming non-operational. In this case, the monitoring application server 760 may infer that the drone device was smashed by the intruder and control other drone devices based on the inference. For instance, after inferring a smash event, the monitoring application server 760 may control operation of other drone devices to maintain distance from the intruder by only flying high overhead.

In some implementations, the monitoring application server 760 may determine battery power available for each of the drone devices 780 and 782 and coordinate operation of the drone devices 780 and 782 based on available battery power. In these implementations, the drone devices 780 and 782 may report battery power remaining to the monitoring application server 760 and the monitoring application server 760 may determine a subset of the drone devices 780 and 782 to deploy based on the battery power information. For instance, the monitoring application server 760 may select to initially deploy the drone device with the most available battery power to allow the other drone devices to charge while the selected device assists with monitoring. Once the battery power for the selected device falls below a threshold, the monitoring application server 760 may return the selected device to a charging station and select the drone device with the presently highest available battery power to resume the monitoring options being performed. The monitoring application server 760 may cycle through all of the drone devices 780 and 782 in an intelligent manner that best leverages the battery power available. If the battery power of a device becomes too low to effectively operate as a navigating device, the monitoring application server 760 may control the drone device to remain stationary and act as a stationary camera or other sensor to still assist with monitoring, although the added benefit of navigation no longer exists.

In addition to battery, the monitoring application server 760 may select the drone device to deploy and what action to take based on the sensor that triggered the event, a time of day, and a state of the system. For instance, if the monitoring application server 760 detects an unusual motion sensor event, the monitoring application server 760 may select the nearest drone device to navigate to an area of the property where motion was detected and investigate. Alternatively, if the monitoring application server 760 detects a critical alarm event (e.g., a security breach of a system armed stay, a fire alarm, a carbon monoxide alarm, etc.), the monitoring application server 760 may deploy all drone devices 780 and 782 at any time of the day. If the monitoring application server 760 detects an intrusion breach, the monitoring application server 760 may assign some devices to "attack" the intruder by disrupting the purpose of the intruder and collecting identifying information for the intruder and assign some devices to search for other users in the property. The selected devices and actions taken may vary based on sensor data, time of day, and the state of the monitoring system.

In some implementations, the system 700 allows drone base station operators, first responders, and/or users of the property to interact with and control the drone devices 780 and 782. In these implementations, a drone base station operator, first responder, or user of the property may provide input to control the drone devices 780 and 782 in a manner that best assists with monitoring and investigation of detected events. For instance, the drone base station operator, first responder, or user of the property may remotely control navigation of the drone devices 180 and 782. The drone base station operator, first responder, or user of the property also may provide general commands related to actions the drone devices 780 and 782 are designed to take. In response to these general commands, the drone devices 780 and 782 may automatically perform the desired actions, such as following an instruction to explore the property or following an instruction to navigate to an upstairs bedroom.

In some implementations, the drone devices 780 and 782 may periodically perform test sequences to ensure the drone devices 780 and 782 will operate correctly if needed. In these examples, the drone devices 780 and 782 may periodically navigate predefined navigation patterns used to investigate the property and/or may navigate around the property in a scanning sequence. The drone devices 780 and 782 may determine whether the test sequences perform correctly or whether an error occurs that prevents full investigation of the property. To the extent an error occurs, the drone devices 780 and 782 report the error and enable a user of the property or a technician to correct the error prior to a time when the drone devices 780 and 782 would be needed for safety monitoring.

The monitoring application server 760 also may arrange the test sequences to occur during periods of time that are convenient for users of the property. For example, the monitoring application server 760 may assess sensor data at the property and determine a time period in which the property is unoccupied and unlikely to be occupied until the test sequences complete. In this example, the monitoring application server 760 waits until the preferred time period to initiate test sequences for one or more of the drone devices 780 and 782.

In some implementations, the drone devices 780 and 782 may be used to provide a critical alert to a user in the property or attempt to wake a sleeping person as appropriate. In these examples, none of the users may be responding to a critical alert and, in response, the monitoring application server 760 may control the drone devices 780 and 782 to search for a person in the property and provide the critical alert very close to an identified person in a manner that is highly likely to gain the person's attention to the critical alert. In the event that the person appears to be sleeping in the property, the drone devices 780 and 782 may attempt to wake the person by providing loud input very near the person and/or by making contact with the person. In this regard, the drone devices 780 and 782 may be useful in waking a sleeping person when a fire or carbon monoxide alarm has been detected and the person needs to leave the property. The drone devices 780 and 782 also may determine when a person is nonresponsive (e.g., unconscious) and may be need of immediate assistance. Also, the drone devices 780 and 782 may serve as an alarm clock for critical meetings based on a person having trouble waking up using traditional alarm clocks.

In some implementations, the drone devices 780 and 782 may be operated independently of the monitoring application server 760. For instance, in such implementations, the drone devices 780 and 782 may be operated locally by a community-based organization (e.g., neighborhood watch) that provides local security and surveillance of a neighborhood without a security provider. In such implementations, the drone devices 780 and 782 may be configured to exchange communications with each of the monitor control units 710 associated with the properties within the neighborhood. In this regard, the drone devices 780 and 782 may be used to provide surveillance of properties within a neighborhood without the use of a security provider.

In some implementations, the monitoring station server 770 may perform a verification operation prior to deploying the drone devices 780 and 782 to a property location in response to a detecting a potential security event. For instance, the monitoring station server 770 may deploy the drone devices 780 and 782 routinely to capture video footage of the neighborhood over particular time periods (e.g., weekly, monthly, etc.). In such instances, the video footage may be used to determine common routines within the property such as time periods of elevated traffic patterns, or susceptible locations such that during a potential security event, the monitoring station server 770 may calculate a likelihood that the potential security event is an actual security event based on video footage from routine surveillance. For example, the monitoring station server 770 may also call individuals associated with the location or gather information and then transmit the information to first responders. In other instances, if the drone devices 780 and 782 determines that the potential security event at a particular location is a false positive, than the user at the location may have an option to send the drone devices 780 and 782 back to the drone base station.

In other implementations, in addition to performing routine surveillance of the neighborhood, the monitoring station server 770 may access additional information about the neighborhood from third party sources. For example, the monitoring station server 770 may use the data to generate a statistical model that is used to determine whether the potential security event is an actual security event. In this regard, the statistical model may use attributes associated with the community to verify the validity of a security event to prevent false positives and conserve energy associated with deploying the drone devices 780 and 782 to a particular location.

In some implementations, the system 700 may be used to detect power outages within a neighborhood. For example, in response to detecting decreased power use, loss of cellular coverage, or change in user behavior at a particular location within the neighborhood, the monitoring station server 770 may deploy the drones 780 and 782 to gather information that may indicate whether maintenance service may be needed to resolve an infrastructure problem. In this regard, the system 700 may leverage the detection and surveillance capabilities of the monitoring station server 770 and the drone devices 780 and 782 to reduce neighborhood infrastructure maintenance costs.

Figure 8:
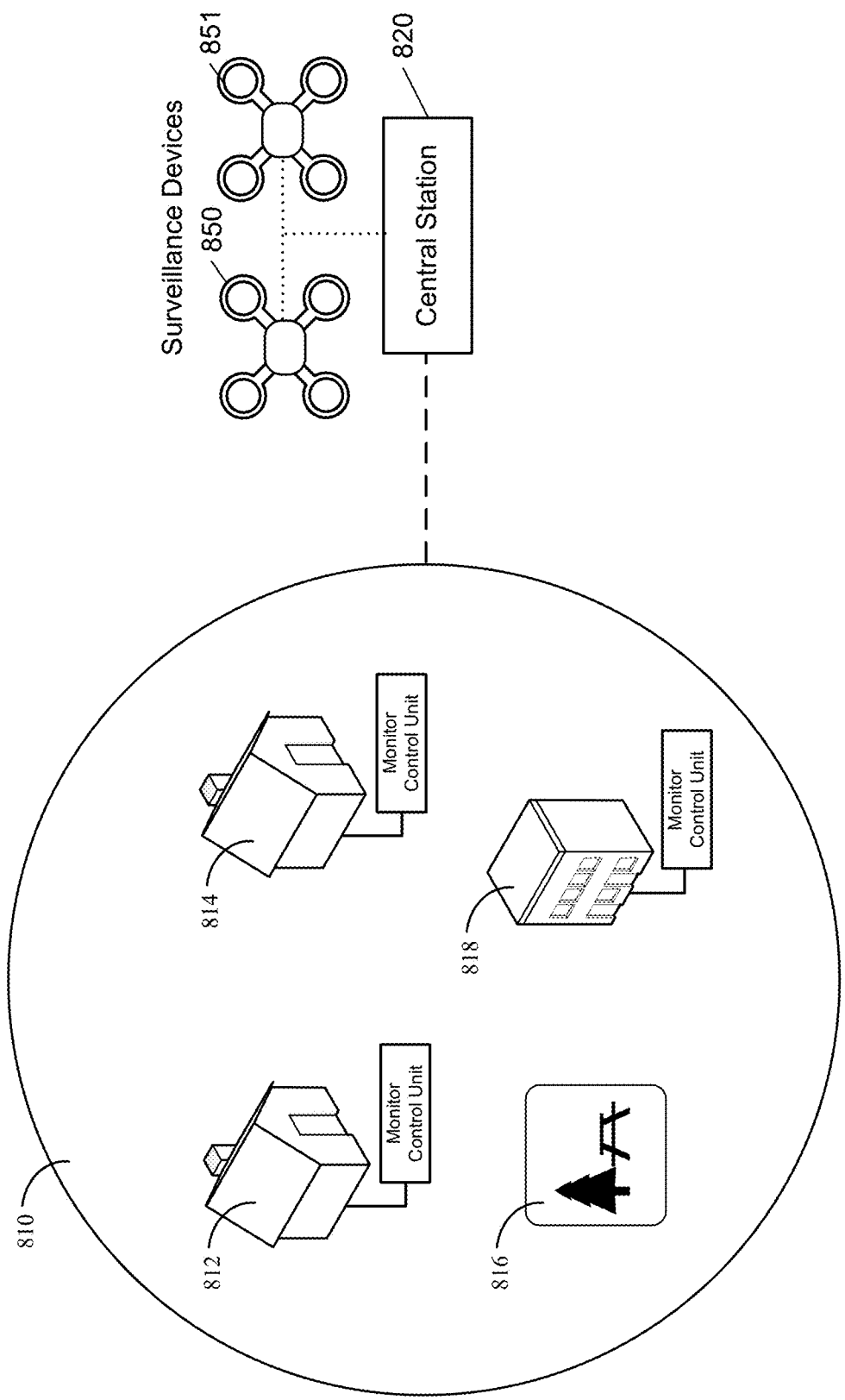
FIG. 8 is a contextual diagram of an example of a community-based drone augmented surveillance system that performs surveillance of a neighborhood.

FIG. 8 is a contextual diagram of an example of a community-based drone augmented surveillance system that performs surveillance of a neighborhood. For example, the neighborhood 810 may be a municipality with geographic boundaries specified by, for example, local laws, service providers, or postal zip codes. The properties that are included in the neighborhood 810 may be monitored by drone devices 850 and 851 located at a drone base station 820. In some instances, the drone devices 850 and 851 correspond to the drone devices 180 and 182, respectively, as described previously with respect to FIG. 7.

The neighborhood 810 may include different types of properties such as, for example, private homes (e.g., properties 812 and 814), public places such as parks (e.g., property 816), office buildings (e.g., property 818), or other types of properties that are commonly included within a municipality. The neighborhood 810 may also include the drone base station 820, which provides monitoring and surveillance of the properties within the neighborhood 810. In some instances, the neighborhood 810 may house the monitoring station server 770, as discussed previously with respect to FIG. 7.

The drone base station 820 may be used to coordinate the operation, movement, deployment, of the drone devices 850 and 851. For example, in some instances, the drone base station 820 may house thousands of drone devices that may be used for different purposes (e.g., surveillance, safety monitoring, alarm response, information extraction, etc.). In such instances, the central alarm station may include computing devices that use cloud-based software to gather information related to the drone devices 850 and 851, events or activities taking place within the neighborhood 810, external conditions (e.g., weather and traffic conditions) of various locations within the neighborhood 810, and operational statuses of key organizations (e.g., first responders, law enforcement, hospitals) to management deployment of the drone devices 850 and 851. In this regard, the drone base station 820 may aggregate data from various sources to effectively and efficiently operate the drone devices 850 and 851 with respect to neighborhood 810.

In some implementations, the drone base station 820 may include an elevated platform to house the drone devices 850 and 851. For example, the elevated platform may include features such as, for example, cellular monitoring, and pneumatic control to open roof of the drone base station 820. In some instances, the drone base station 820 may additionally include computing devices that gather information related to the deployment paths of the drone devices 850 and 851. For example, the computer devices may track the patterns of the drone devices 850 and 851 to determine fastest or most energy-efficient routes to get to particular locations within the neighborhood 820. In other examples, the computer devices may extract the data from the drone devices 850 and 851 after a deployment while the drone devices 850 and 851 are being charged at the drone base station 820.

The drone devices 850 and 851 may be stored at the drone base station 820. For example, in some instances, the drone base station 820 may include the charging stations 190 and 192 as described with respect to FIG. 7. In such instances, the drone devices 850 and 851 may be deployed from the drone base station 820 to the locations of the properties 812, 814, 816, or 818. For example, the drone devices 850 and 851 may be deployed to the location of one of the properties 812, 814, 816, or 818 in response to a detected security event that creates a safety hazard at the location.

In some implementations, the drone devices 850 and 851 may be used for applications other than ensuring safety within the neighborhood 810. For instance, the drones 850 and 851 may be used to help local authorities search for particular objects, lost kids, wandering or lost mentally disabled persons, lost pets, individuals that are suspected to be located within the neighborhood 820, or the like. For example, the drone devices 850 and 851 may be used to search for cars and other inanimate objects of interest and identify outward attributes associated with objects (e.g., license plates on vehicles). In other instances, the drone devices 850 and 851 may be used to collect information from such searching operations and perform data aggregation techniques to calculate trends associated with the neighborhood 820. For example, the drone devices 850 and 851 may be deployed during rush hour traffic to determine routine traffic volumes entering and exiting the boundaries of the neighborhood 820, distinguish between cars that are owned by residents and non-residents, determine relevant information to collect based on previous security events, provide a list of strange vehicles, or cross-reference the collected information against public databases to determine other types of potential safety risks.

In some implementations, the drone devices 850 and 851 may be used to selectively monitor certain properties within the neighborhood 810 while not performing surveillance on other properties within the neighborhood 810. For example, in some instance, the users of the properties within the neighborhood 810 may create user accounts that specify particular types of surveillance operations that they would like to receive. In such instances, an account number may be associated with the properties on a map of the neighborhood 810 to enable the drone devices 850 and 851 to identify properties that are associated with account numbers. For example, if a user account associated with a particular property specifies that no recording of the property, then the drone devices 850 and 851 may adjust the route taken during a surveillance operation, based on the map of the neighborhood 810 to avoid recording the particular property.

In some implementations, the drone devices 850 and 851 may be operated along with an aberration engine that determines the occurrence of an aberration event within the neighborhood 810. For example, the drone devices may be deployed to a particular location where the aberration event takes place. In this regard, the drone devices 850 and 851 may be used to investigate events that may cause potential problems within the neighborhood 810.

In some implementations, the drone devices 850 and 851 may be used in various commercial broadcasting environments within the neighborhood 810. For example, the drone devices 850 and 851 may be used in public events (e.g., sporting events, concerts) where cameras are used to capture video footage of the public events. In such implementations, the drone devices 850 and 851 may be used as a connected camera system that broadcasts footage of the public events to the drone base station 820.

FIG. 9 is a flowchart of an example of a process for deploying drones in response to a detection of a potential emergency event.

The process 900 may begin when a server such as a monitoring application server 330 receives 910 an emergency event notification associated with a property (910). For example, a server such as a monitoring application server 330 may receive an emergency event notification from one or more monitor control units such as monitor control unit 316*a* that are each located within a respective property. Each emergency event notification may be generated by a monitor control unit 316*a* based on data received from one or more sensors located throughout the property 316 associated with the monitor control unit 316*a*. The emergency event notification may be indicative of an existence of an emergency event at the property associated with the monitor control unit that transmitted the emergency event notification.

At 920, the server such as monitoring application server 330 may determine a type of emergency and a location based on the received emergency event notification. For example, a server such as monitoring application server 330 may initially determine the type of emergency event indicated by the emergency event notification and identify the location of the property where the emergency event is taking place. The server may determine the type of emergency event by obtaining data in the emergency event notification, and mapping the obtained data to one or more emergencies. For example, obtained data may include, for example, an emergency event identifier comprised of one or more numbers, alphabetic characters, or both that can be mapped to a particular emergency. The mapping between emergency event identifiers and emergencies may be a one-to-one mapping such that each emergency event identifier is associated with a particular type of emergency. Alternatively, or in addition, the obtained data may include a sensor identifier that can be used to determine the type of emergency. For example, the server may determine that a sensor identifier corresponds to a power sensor. Accordingly, an emergency event generated by the power sensor may be determined to be a power outage. Implementations that use a sensor identifier to determine the type of emergency may not need to include an emergency event identifier whose sole purpose is to identify an emergency type, as the sensor identifier can be used for this purpose, as described above.

The server such as monitoring application server 330 may also determine the location of the emergency event based on the emergency event notification. For example, in one implementation, the emergency event notification may include location data such as a GPS location, a street address, or the like. Alternatively, however, the location of an emergency event may be determined without an explicit inclusion of a location in the emergency event notification. In such implementations, the location of each sensor may be registered and stored in the monitoring application server at the time of installation (or at some point in time after installation). Accordingly, an emergency event notification may only include a sensor identifier, which the server can use to retrieve the location where the sensor that generated the alarm event notification is located.

At stage 930, the server such as monitoring application server 330 may identify one or drone devices that can be deployed to the location associated with the emergency event. In one implementation, the server may identify one or more drones that are equipped with the capabilities to respond to the emergency event. For example, if the detected emergency is a fire emergency, the server may identify one or more drones 355, 357 that are equipped to fight a fire. Alternatively, or in addition, the server may identify whether one or more drones 359, 360 that are within a threshold distance from the location 316 that is associated with the emergency event. For example, the monitoring application server 330 may determine if one more previously deployed drones are located within a particular distance from the property where the emergency event is taking place.

The process may conclude at 940 with the server transmitting an instruction to another server at a drone base station, which instructs the server at the drone base station to deploy the identified one or more drone devices to the property location associated with the emergency event. For example, the monitoring application server 330 may transmit a signal to the monitoring station server 320*a* to re-deploy the one or more identified drones 359, 360 to the location of the property where the alarm event is taking place. The monitoring station server 320*a* may then transmit an instruction including the location of the property and details about the type of emergency event to the one or more drone devices 359, 360.

Figure 10:
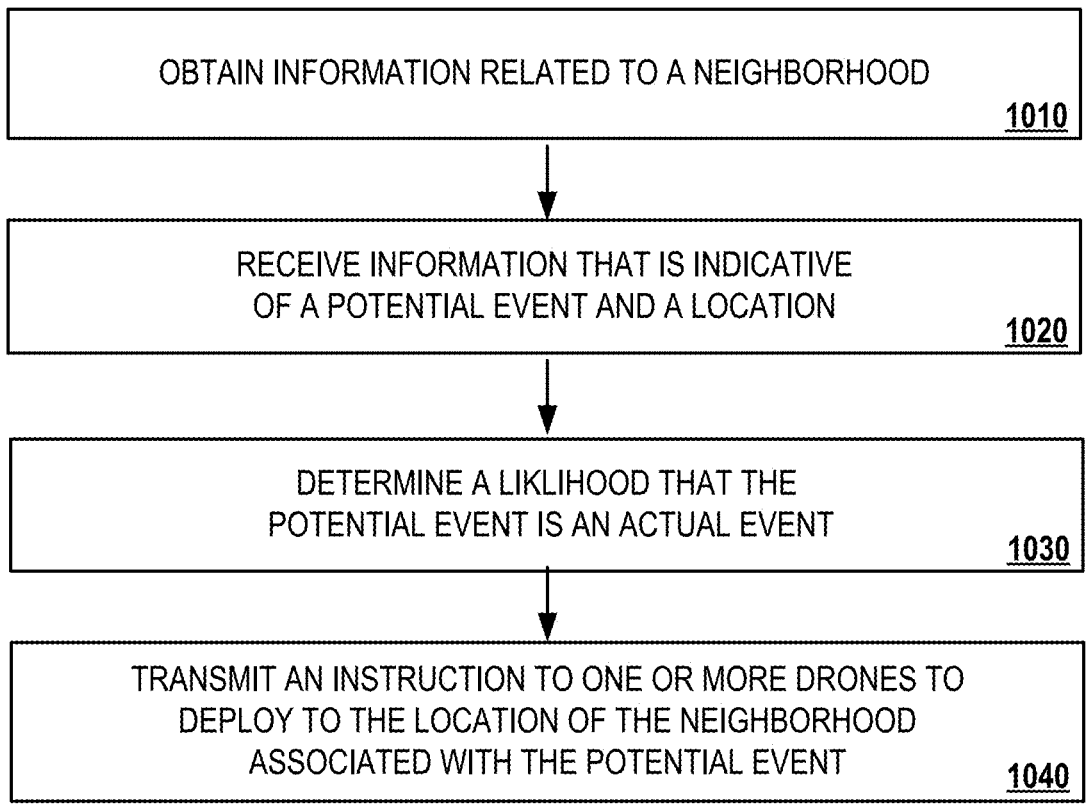
FIG. 10 is a flowchart of an example of a process for deploying drones in response to a detection of a potential event using information indicative of common routines of the neighborhood residents.

FIG. 10 is a flowchart of an example of a process 1000 for deploying drones in response to a detection of a potential event using information indicative of common routines of the neighborhood residents.

The process 1000 may begin by obtaining 1010 information related to the routines of a neighborhood over time. A server such as the monitoring station server or monitoring application server may instruct one or more drones to periodically gather information related to the routines of residents within the neighborhood. The gathered information may include, for example, video recordings or images of traffic patterns, video recordings or images of sidewalk traffic patterns, video recordings or images of common areas such as parks, or the like. Such information may be accrued and stored overtime in order to create a library of historical information that is indicative of normal routines, characteristics, or the like of a neighborhood.

At 1020, the server may receive information that is indicative of a security event or emergency event and a location. For example, the server may receive a security event notification or an emergency event notification that is indicative of a potential event. After receiving the indication of a potential event and location, the server may determine 1030 the likelihood that the potential event is an actual security event or an actual emergency event. Determining 1030 whether a potential event is an actual security event or actual emergency event may include comparing one or more types of obtained historical information related to current information related to the property. For example, the determining 1030 stage may include comparing (i) a historical video showing the common routine in a particular portion of a neighborhood on a particular day of the week at particular time to (i) a current video of the same particular portion of the neighborhood on the same day of the week at the same time. If the comparison shows that the historical video is sufficiently different the current video, such a result may be supportive of the existence of a security event. This is because the normal routine of a neighborhood may be disrupted when faced with responding to a security event or an emergency event. In response to determining that the potential event is an actual security event or an actual emergency event, transmitting 1040 a deployment instruction to one or more drones to deploy drones to the location of the neighborhood associated with the potential event.

Figure 11:
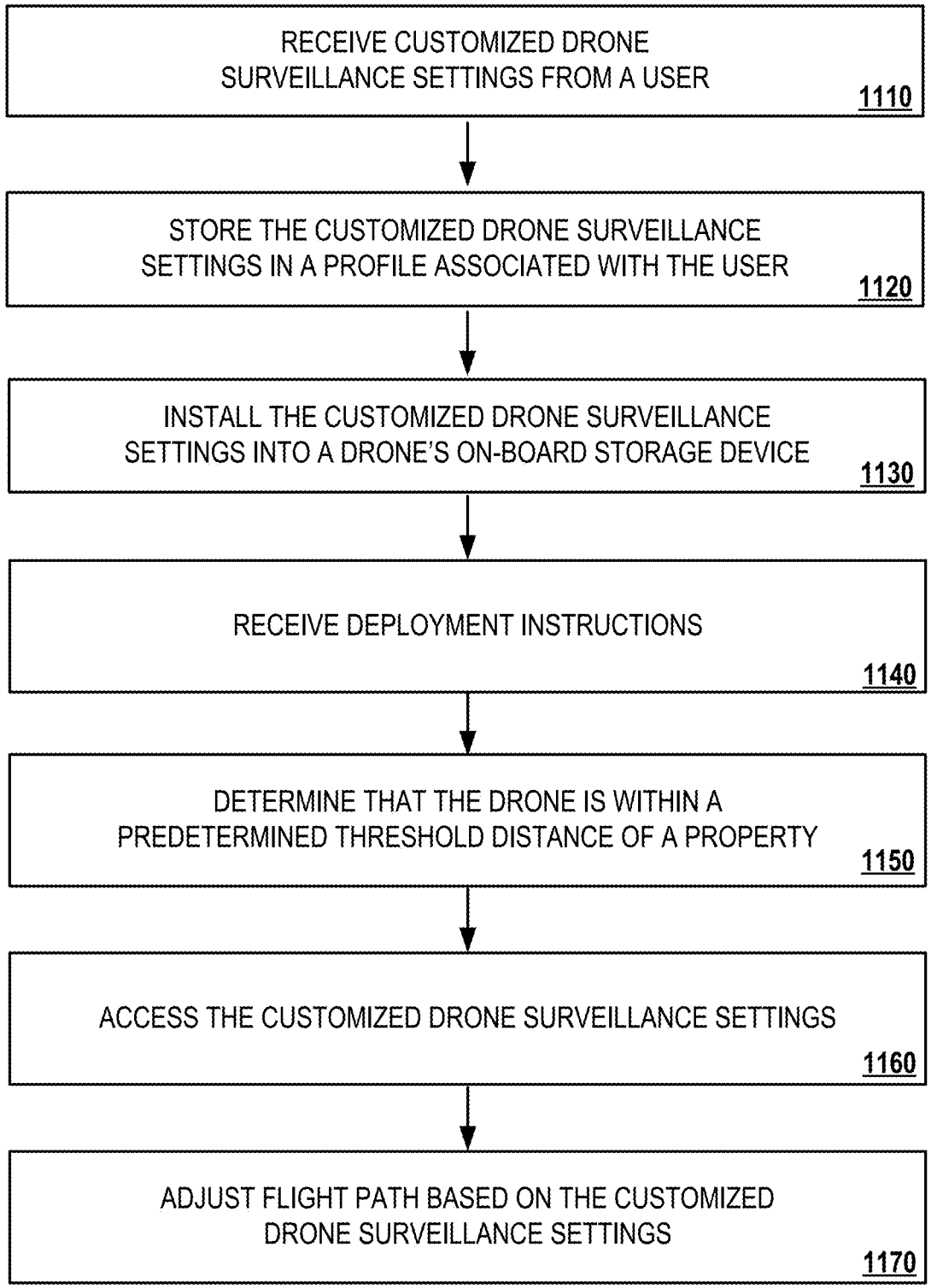
FIG. 11 is a flowchart of an example of a process for deploying drones in accordance with customized drone surveillance settings.

FIG. 11 is a flowchart of an example of a process 1100 for deploying drones in accordance with customized drone surveillance settings.

The process 1100 may begin when a server such as the monitoring application server or a monitoring station server receives 1110 customized drone surveillance settings from a resident of a neighborhood. The server may store 1120 the customized drone surveillance setting in the resident's user profile. The customizable drone surveillance settings may include, for example, drone surveillance preferences such as (i) whether a drone can (or cannot) record video of the resident's property, (ii) whether a drone can (or cannot) capture still images of the property, (iii) whether a drone can (or cannot) perform thermal imaging of the property, (iv) whether a drone can (or cannot) enter the within a predetermined distance of the resident's housing structure, (v) whether a drone can (or cannot) cross the resident's property line, (vi) whether a drone can (or cannot) enter the airspace above the resident's property, or the like. In some implementations, the customizable drone surveillance settings may be conditional. For instance, a resident may set one or more customizable drone surveillance settings which can be overridden in the event a predetermined condition is detected.

Prior to deployment, the server may obtain the stored user profiles for each resident in the neighborhood. The obtained set of stored user profiles may be installed 1130 into a drone's on-board memory prior to the drone's receipt of surveillance deployment instructions. The drone may receive 1140 deployment instructions to surveil the resident's neighborhood. The deployed drone may begin to travel along a predetermined flight path to perform routine surveillance of the resident's neighborhood. The drone may determine 1150 when the drone arrives within a predetermined threshold distance of a resident's property that is associated with one or more customized drone surveillance parameters. In response to determining that the drone is within a predetermined threshold distance of a resident's property, the drone may access 1160 the resident's customized drone surveillance settings. The drone may adjust the drone's predetermined surveillance flight path, alter the capture settings of the drone's surveillance equipment tools, or a combination thereof, based on the resident's customized drone surveillance parameters.

The described systems, methods, and techniques may be implemented in digital electronic circuitry, computer hardware, firmware, software, or in combinations of these elements. Apparatus implementing these techniques may include appropriate input and output devices, a computer processor, and a computer program product tangibly embodied in a machine-readable storage device for execution by a programmable processor. A process implementing these techniques may be performed by a programmable processor executing a program of instructions to perform desired functions by operating on input data and generating appropriate output. The techniques may be implemented in one or more computer programs that are executable on a programmable system including at least one programmable processor coupled to receive data and instructions from, and to transmit data and instructions to, a data storage system, at least one input device, and at least one output device. Each computer program may be implemented in a high-level procedural or object-oriented programming language, or in assembly or machine language if desired; and in any case, the language may be a compiled or interpreted language. Suitable processors include, by way of example, both general and special purpose microprocessors. Generally, a processor will receive instructions and data from a read-only memory and/or a random access memory. Storage devices suitable for tangibly embodying computer program instructions and data include all forms of non-volatile memory, including by way of example semiconductor memory devices, such as Erasable Programmable Read-Only Memory (EPROM), Electrically Erasable Programmable Read-Only Memory (EEPROM), and flash memory devices; magnetic disks such as internal hard disks and removable disks; magneto-optical disks; and Compact Disc Read-Only Memory (CD-ROM). Any of the foregoing may be supplemented by, or incorporated in, specially designed application-specific integrated circuits (ASICs).

It will be understood that various modifications may be made. For example, other useful implementations could be achieved if steps of the disclosed techniques were performed in a different order and/or if components in the disclosed systems were combined in a different manner and/or replaced or supplemented by other components. Accordingly, other implementations are within the scope of the disclosure.

What is claimed is:

1. A method performed by one or more computing devices, the method comprising:

obtaining data indicating an emergency event detected at a property located within a geographic region, wherein the geographic region is associated with a set of drones configured to service a set of properties located within the geographic region;

determining, based on obtaining the data, one or more characteristics of the emergency event;

selecting, based on the one or more characteristics, a drone from among the set of drones, wherein the drone is selected to perform a surveillance operation related to the property; and causing the drone to perform the surveillance operation related to the property.

2. The method of claim 1, wherein:

the one or more characteristics comprises a location of the emergency event within the property;

the method further comprises determining respective proximities of drones included in the set of drones to the location of the emergency event within the property; and the drone is selected to perform the surveillance operation based on the respective proximities of the drones included in the set of drones.

3. The method of claim 1, wherein:

the one or more characteristics comprises a type of emergency event;

the method further comprises mapping the type of event to one or more drone capabilities; and the drone is selected to perform the surveillance operation based on mapping the type of event to the one or more drone capabilities.

4. The method of claim 3, further comprising:

obtaining second data identifying one or more first sensors that detected the emergency event; and mapping the second data to the type of emergency event of the emergency event.

5. The method of claim 1, wherein the emergency event is detected by a sensor located within the property.

6. The method of claim 5, wherein the sensor comprises a power sensor, a contact sensor, a glass break sensor, a motion sensor, a carbon monoxide sensor, a smoke sensor, a temperature sensor, or a water sensor.

7. The method of claim 1, further comprising providing a notification identifying the emergency event for output to a user device associated with the property.

8. A system comprising:

one or more computing devices; and one or more storage devices storing instructions that cause the one or more computing devices to perform operations comprising:

obtaining data indicating an emergency event detected at a property located within a geographic region, wherein the geographic region is associated with a set of drones configured to service a set of properties located within the geographic region;

determining, based on obtaining the data, one or more characteristics of the emergency event;

selecting, based on the one or more characteristics, a drone from among the set of drones, wherein the drone is selected to perform a surveillance operation related to the property; and causing the drone to perform the surveillance operation related to the property.

9. The system of claim 8, wherein:

the one or more characteristics comprises a location of the emergency event within the property;

the operations further comprise determining respective proximities of drones included in the set of drones to the location of the emergency event within the property; and the drone is selected to perform the surveillance operation based on the respective proximities of the drones included in the set of drones.

10. The system of claim 8, wherein:

the one or more characteristics comprises a type of emergency event;

the operations further comprise mapping the type of event to one or more drone capabilities; and the drone is selected to perform the surveillance operation based on mapping the type of event to the one or more drone capabilities.

11. The system of claim 10, wherein the operations further comprise:

obtaining second data identifying one or more first sensors that detected the emergency event; and mapping the second data to the type of emergency event of the emergency event.

12. The system of claim 8, wherein the emergency event is detected by a sensor located within the property.

13. The system of claim 12, wherein the sensor comprises a power sensor, a contact sensor, a glass break sensor, a motion sensor, a carbon monoxide sensor, a smoke sensor, a temperature sensor, or a water sensor.

14. The system of claim 8, wherein the operations further comprise providing a notification identifying the emergency event for output to a user device associated with the property.

15. At least one non-transitory computer-readable storage device storing instructions that cause one or more processors to perform operations comprising:

obtaining data indicating an emergency event detected at a property located within a geographic region, wherein the geographic region is associated with a set of drones configured to service a set of properties located within the geographic region;

determining, based on obtaining the data, one or more characteristics of the emergency event;

selecting, based on the one or more characteristics, a drone from among the set of drones, wherein the drone is selected to perform a surveillance operation related to the property; and causing the drone to perform the surveillance operation related to the property.

16. The storage device of claim 15, wherein:

the one or more characteristics comprises a location of the emergency event within the property;

the operations further comprise determining respective proximities of drones included in the set of drones to the location of the emergency event within the property; and the drone is selected to perform the surveillance operation based on the respective proximities of the drones included in the set of drones.

17. The storage device of claim 15, wherein:

the one or more characteristics comprises a type of emergency event;

the operations further comprise mapping the type of event to one or more drone capabilities; and the drone is selected to perform the surveillance operation based on mapping the type of event to the one or more drone capabilities.

18. The storage device of claim 17, wherein the operations further comprise:

obtaining second data identifying one or more first sensors that detected the emergency event; and mapping the second data to the type of emergency event of the emergency event.

19. The storage device of claim 15, wherein the emergency event is detected by a sensor located within the property.

20. The storage device of claim 19, wherein the sensor comprises a power sensor, a contact sensor, a glass break sensor, a motion sensor, a carbon monoxide sensor, a smoke sensor, a temperature sensor, or a water sensor.

* * * * *